(12) United States Patent
Schmitt et al.

(10) Patent No.: US 9,198,445 B2
(45) Date of Patent: Dec. 1, 2015

(54) WHEY PROTEIN VEHICLE FOR ACTIVE AGENT DELIVERY

(75) Inventors: Christophe Schmitt, Servion (CH); Lionel Jean René Bovetto, Larringes (CH)

(73) Assignee: Nestec S.A., Vevey (CH)

( * ) Notice: Subject to any disclaimer, the term of this patent is extended or adjusted under 35 U.S.C. 154(b) by 1107 days.

(21) Appl. No.: 12/294,540

(22) PCT Filed: Mar. 27, 2007

(86) PCT No.: PCT/EP2007/052904
§ 371 (c)(1),
(2), (4) Date: Sep. 25, 2008

(87) PCT Pub. No.: WO2007/110422
PCT Pub. Date: Oct. 4, 2007

(65) Prior Publication Data
US 2009/0162485 A1    Jun. 25, 2009

(30) Foreign Application Priority Data
Mar. 27, 2006 (EP) .................................. 06006297

(51) Int. Cl.
| A23C 21/00 | (2006.01) |
| A23J 1/20 | (2006.01) |
| A23L 1/40 | (2006.01) |
| A23F 3/32 | (2006.01) |
| A61K 8/02 | (2006.01) |
| A23F 5/40 | (2006.01) |
| A23J 3/08 | (2006.01) |
| A23L 1/00 | (2006.01) |
| A61K 8/64 | (2006.01) |
| A61Q 19/00 | (2006.01) |

(52) U.S. Cl.
CPC . *A23F 3/32* (2013.01); *A23C 21/00* (2013.01); *A23F 5/40* (2013.01); *A23J 3/08* (2013.01); *A23L 1/0029* (2013.01); *A61K 8/0241* (2013.01); *A61K 8/0275* (2013.01); *A61K 8/0291* (2013.01); *A61K 8/64* (2013.01); *A61Q 19/00* (2013.01); *A23V 2002/00* (2013.01); *A61K 2800/56* (2013.01)

(58) Field of Classification Search
CPC .................. A23V 2250/54252; A61K 8/0291; A61K 8/64; A23C 9/1512; A23C 21/06; A23J 3/08
See application file for complete search history.

(56) References Cited

U.S. PATENT DOCUMENTS

| 5,260,083 | A | 11/1993 | Brain et al. ................... 426/573 |
| 5,350,590 | A | 9/1994 | McCarthy et al. ............ 426/549 |
| 5,451,420 | A | 9/1995 | Brain et al. ................... 426/573 |
| 5,601,760 | A | 2/1997 | Rosenberg ..................... 264/4.1 |
| 5,756,136 | A | 5/1998 | Black et al. ..................... 426/89 |
| 5,882,705 | A | 3/1999 | Sato et al. ........................ 426/41 |
| 6,673,384 | B1 | 1/2004 | Villagran et al. ............. 426/575 |
| 6,757,575 | B1 | 6/2004 | Hu ................................. 700/94 |
| 2002/0051843 | A1 | 5/2002 | Baker et al. ................... 426/583 |
| 2002/0119232 | A1 | 8/2002 | Grazela et al. ................ 426/555 |
| 2004/0062846 | A1 | 4/2004 | Sargent et al. ................ 426/601 |
| 2004/0156979 | A1 | 8/2004 | Villagran et al. ............. 426/656 |
| 2005/0226905 | A1 * | 10/2005 | Tien et al. ..................... 424/439 |
| 2005/0287196 | A1 * | 12/2005 | Cho et al. ...................... 424/450 |

FOREIGN PATENT DOCUMENTS

| EP | 0 180 441 B1 | 5/1986 | |
| GB | 2 063 273 A | 6/1991 | |
| WO | WO 96/38055 A1 | 12/1996 | |
| WO | WO 2005/048998 A1 | 6/2005 | |
| WO | WO 2006034857 A2 * | 4/2006 | ............ A23C 21/00 |

OTHER PUBLICATIONS

Hollar et al., J. Dairy Sci., 1995, 78, 260-267.*
International Search Report and Written Opinion of the International Searching Authority, application No. PCT/EP2007/052904, dated Feb. 18, 2008.
European Search Report, application No. EP 06006297, dated Sep. 13, 2006.
A. A. Reid et l., XP009087731, "Microentrapment of Probiotic Bacteria in a $Ca^{2+}$—Induced Whey Protein Gel and Effects on Their Viability in a Dynamic Gastro-Intestinal Model", Journal of Microencapsulation, vol. 22 (6), pp. 603-619 (2005).
Z. Zhang et al., "Effect of pH and Ionic Strength on Competitive Protein Adsorption to Air/Water Interfaces in Aqueous Foams Made With Mixed Milk Proteins", Colloids and Surfaces B: Biointerfaces, vol. 34, pp. 113-121 (2004).

* cited by examiner

*Primary Examiner* — Kyle Purdy
(74) *Attorney, Agent, or Firm* — K&L Gates LLP

(57) ABSTRACT

The present invention relates to whey protein micelles, a process for the preparation of aggregates of the sane and particularly to their use as a delivery vehicle for active agents in the field of nutrition or cosmetics.

23 Claims, 20 Drawing Sheets

WHEY PROTEIN VEHICLE FOR ACTIVE AGENT DELIVERY

This application is a 371 filing of International Patent Application PCT/EP2007/052904 filed Mar. 27, 2007.

FIELD OF THE INVENTION

The present invention relates to whey protein micelles, particularly to their use as delivery vehicle for active agents in the field of nutrition and/or cosmetics.

BACKGROUND

Delivery systems are known in the art and have been widely used for targeted delivery of drugs in the body in the pharmaceutical industry, for example. Delivery systems are also often found in the form of microcapsules for food processing.

In food applications, with the use of delivery systems, possible undesirable interaction between the added nutraceutical and other components in the food or its environment can be avoided and the location of release of the added component can be manipulated. The appropriate application of delivery system technology enables maximization of food without affecting the taste, aroma or texture thereof. It can impart protection to sensitive food ingredients and enhance the shelf-life and stability of fortified foods.

Delivery systems can also be a key technology with potential for the delivery of dietary bioactive compounds and/or cosmetic agents. In addition, the optimum delivery system should also meet the need for site specific delivery within the gastrointestinal tract, or skin, hair etc, depending on the desired application.

For this purpose, microencapsulation has often been used. Indeed, the encapsulation of flavours and other active agents in a matrix of a food polymer is well known.

For example, EP 0 180 441 B1 teaches the use of whey proteins to encapsulate volatile flavour components. Hydrolysed milk is concentrated by heating and evaporation to 40-50% solids which also results in the encapsulation with the whey proteins.

WO 96/38055 describes the encapsulation of a flavour or active agent in a matrix of whey protein yielding an encapsulation composition which results in the controlled release of the flavour or active agent and which may be incorporated in a yeast-leavened dough without causing a deleterious effect on the rising of the dough.

WO 2005/048998 is concerned with gastro-intestinal tract delivery systems, whereby microcapsules made from protein and carbohydrate are used.

One of the problems encountered with the production of products containing globular proteins in general, and whey protein in particular, however is their limited processability. Indeed, protein molecules when heated, or when subjected to acidic or alkaline environment or in the presence of salts tend to lose their native structure and reassemble in various random structures such as gels, for example.

In the Proceedings of the Second International Whey Conference, Chicago, October 1997, reported in International Dairy Federation, 1998, 189-196, Britten M. discusses heat treatments to improve functional properties of whey proteins. A process for producing whey protein micro-particle dispersion at 95° C. is described.

Sato et al. in U.S. Pat. No. 5,882,705 obtained micellar whey protein by heat treating a hydrolysed whey protein solution. The micellar whey protein are characterised by an irregular shape.

The encapsulation systems of the prior art, therefore, have been shown to be poorly effective in the controlled release of a flavour or similar agents, insofar as they partially consist of globular protein and are therefore prone to structural modification upon heating, exposure to salts and/or subjection to acidic or alkaline environment.

Thus, there remains a need for a delivery system composition which enables controlled release of a given agent. In addition, advanced food and cosmetic technology requires particularly designed products, such that the active ingredients contained in the delivery system are protected from environmental stress such as UV radiation, light, oxygen, humidity and temperature.

Accordingly, the object of the present invention is to improve the usability of whey proteins as delivery system in a wide range of applications.

SUMMARY OF THE INVENTION

Accordingly, this object is achieved by means of the features of the independent claims. The dependent claims develop further the central idea of the present invention.

To achieve this object, a method for the preparation of aggregates of protein micelles and active agent is proposed, in a first aspect, which comprises the first step of dispersing whey protein micelles and the active agent in a solvent, and the second step of evaporating the solvent.

According to a second aspect of the invention, a method comprising the steps of dispersing native whey proteins and an active agent in an aqueous solution and denaturing the whey protein to whey protein micelles and forming an aggregate of whey protein micelles and the active agent is provided.

An alternative method for preparing aggregates of protein and an active agent comprising the step of mixing a whey protein micelle powder with an active agent falls under another aspect of the invention.

The aggregates obtainable by any of those methods form part of the invention according to another aspect thereof.

According to a further aspect, the invention provides aggregates comprising whey protein micelles and active agent associated with said whey protein micelles.

Food or cosmetic products containing these aggregates also fall under an aspect of the present invention.

Further, the use of whey protein micelles as a vehicle for delivering an active agent, and the use thereof in food and cosmetic applications constitute further aspects of the present invention.

Finally, a complex for active agent delivery comprising whey protein micelles and said active agent is provided by the present invention.

FIGURES

The present invention is further described hereinafter with reference to some preferred embodiments shown in the accompanying figures in which.

Whey protein micelles are obtained at pH 4.25 (positively charged with a zeta potential around +25 mV) and at pH 6.0 (negatively charged with a zeta potential around −30 mV). Z-averaged hydrodynamic diameter of the micelles was 229.3 nm at pH 4.25 and 227.2 nm at pH 6.0.

The corresponding micrographs of the micelles obtained by TEM after negative staining are shown. Scale bars are 1 µm.

Figure 7:
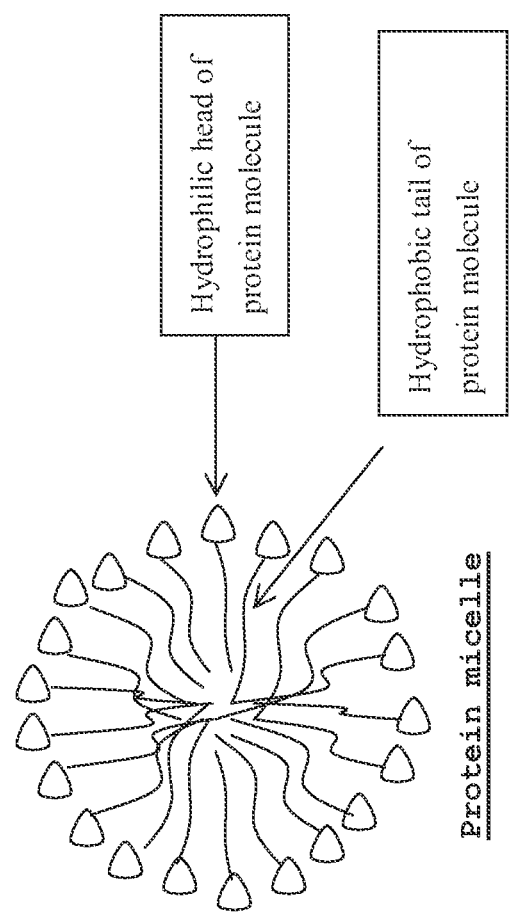

FIG. 7 shows a highly schematic structure of a whey protein micelle.

Figure 8:
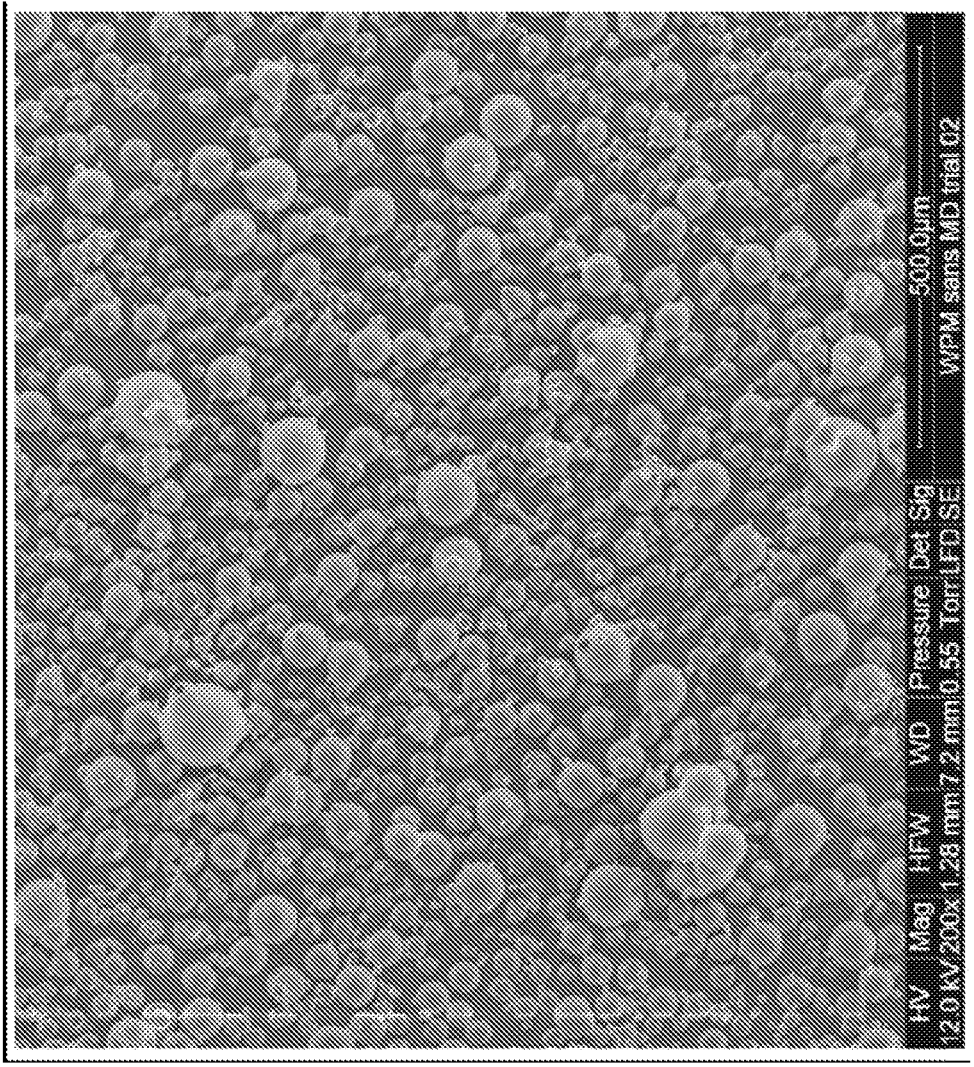

FIG. 8 shows a SEM (Scanning electron microscopy) micrograph of a whey protein micelle powder obtained after spray drying of a 20% protein content dispersion after microfiltration.

Figure 9:
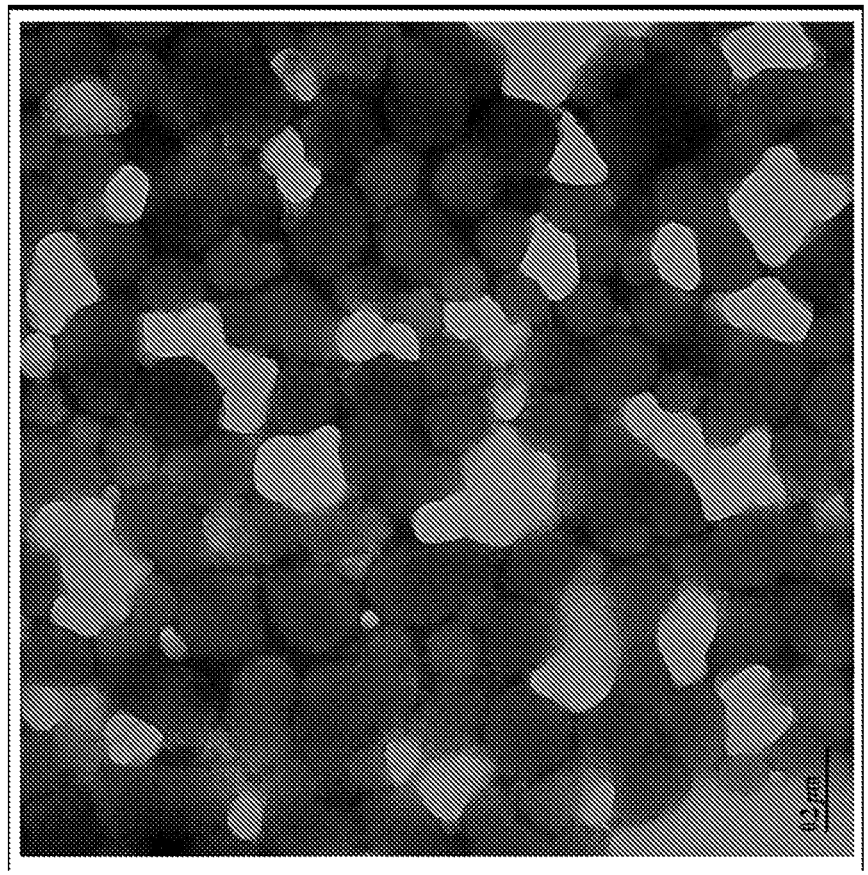

FIG. 9 is a negative staining TEM micrograph of a whey protein micelles dispersion obtained at 4% protein content.

Figure 10:
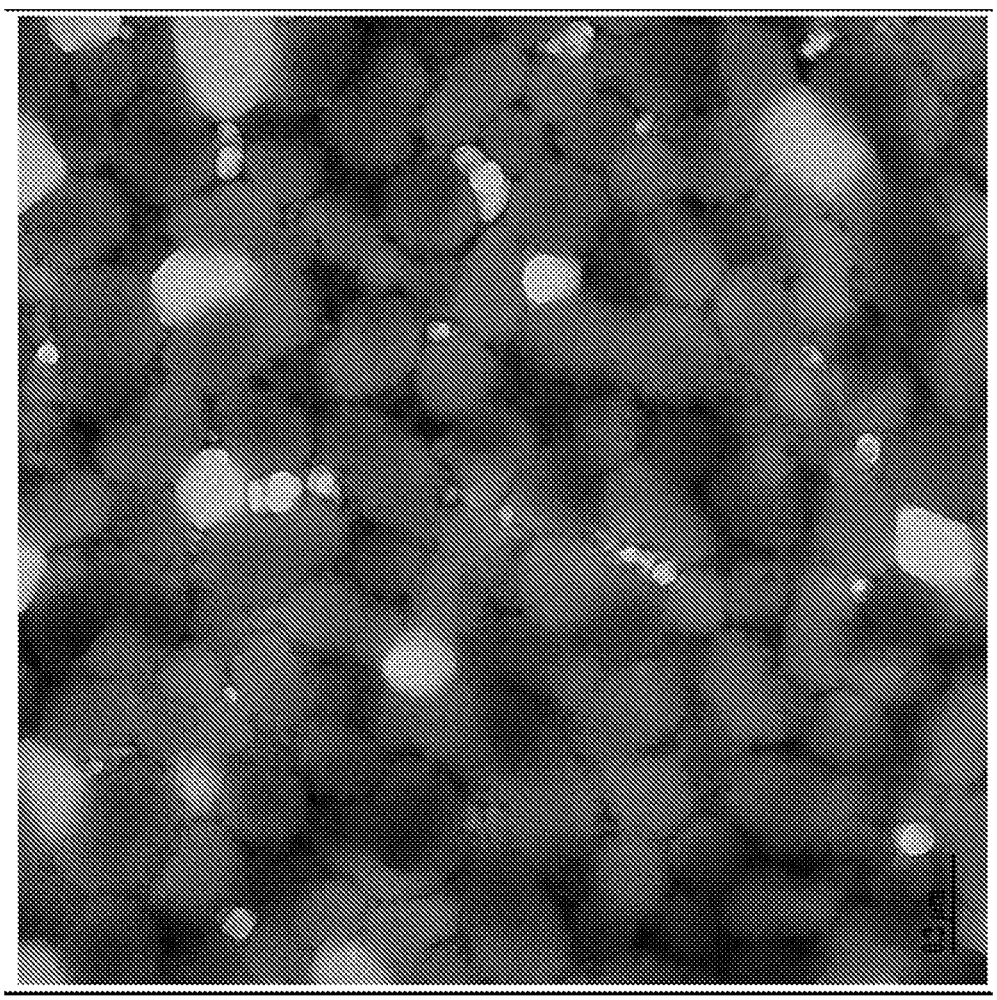

FIG. 10 is a negative staining TEM micrograph of a whey protein micelle dispersion obtained at 20% protein content after microfiltration.

Figure 11:

FIG. 11 shows the heat stability of a whey protein micelle dispersion obtained at 10% protein content after microfiltration at pH 7.0 in presence of NaCl after heating at 85° C. for 15 min.

Figure 12:
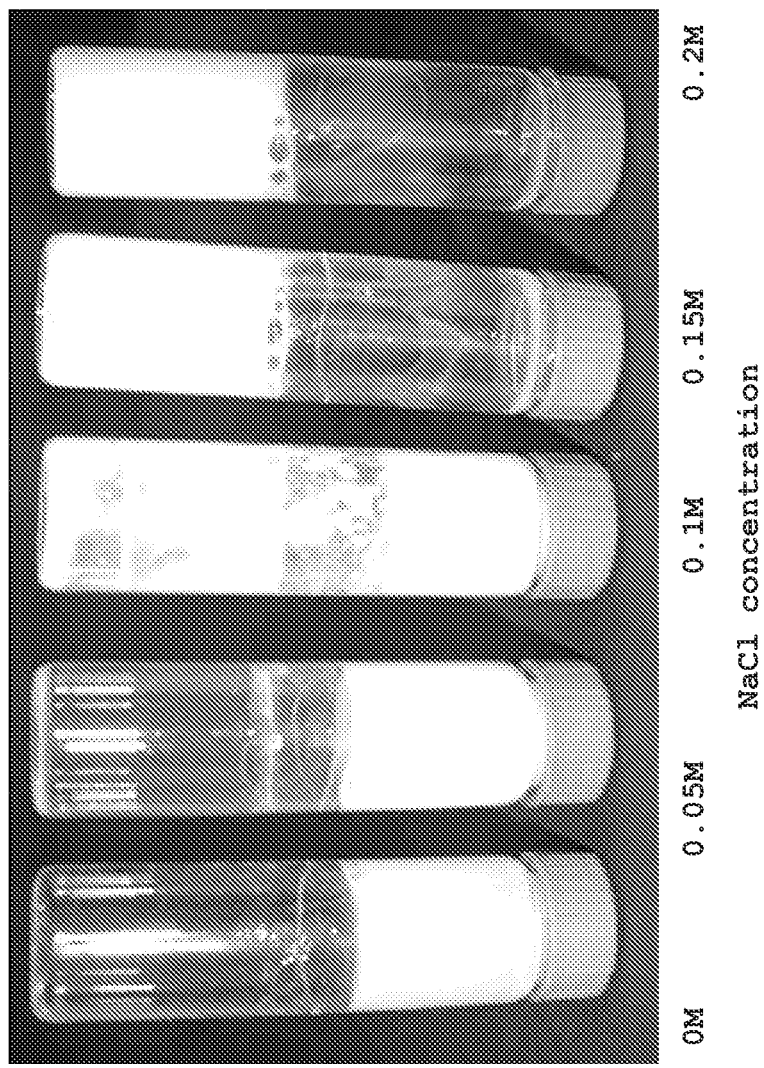

FIG. 12 shows the heat stability of a whey protein dispersion obtained at 4% protein content at pH 7.0 in presence of NaCl after heating at 85° C. for 15 min.

Figure 13:
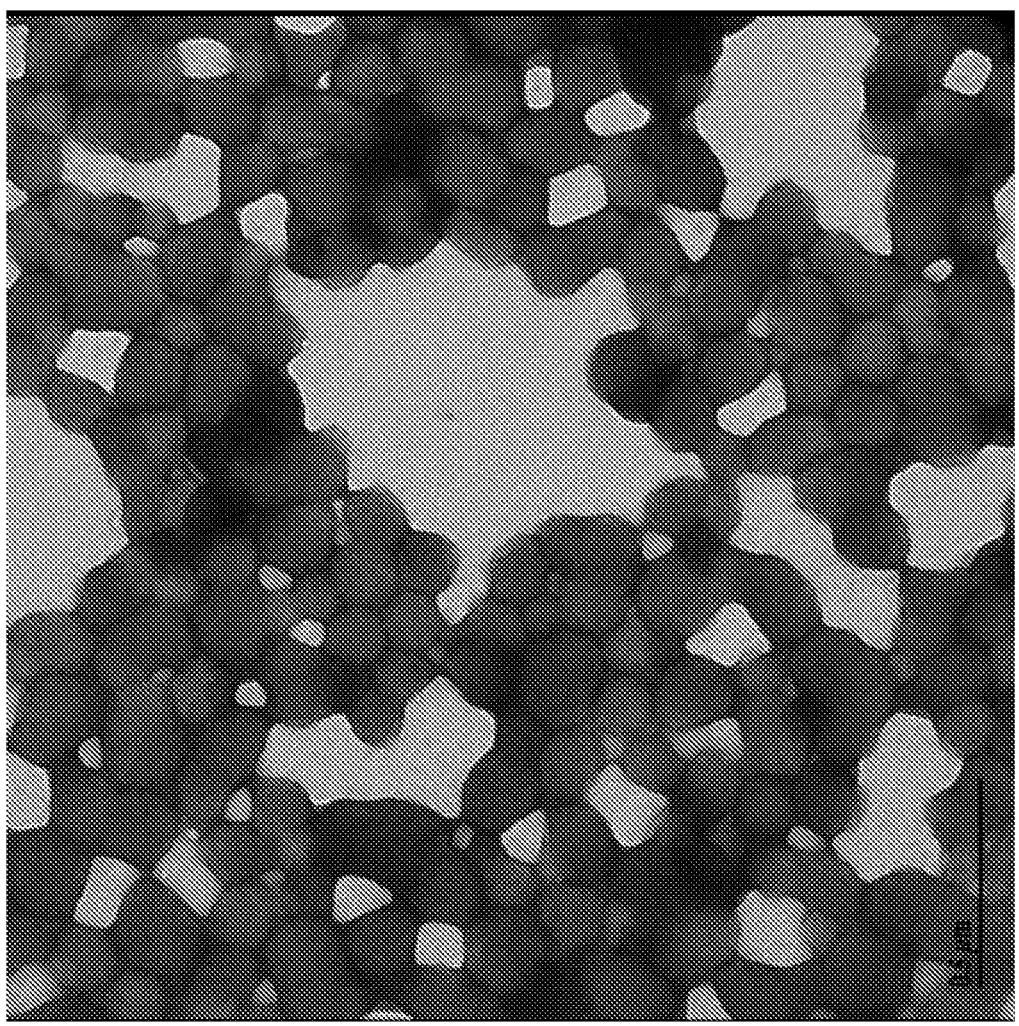

FIG. 13 is a negative staining TEM micrograph from a 4% whey protein micelles dispersion based on a pure whey protein micelle spray dried powder after dispersion at 50° C. in deionised water.

Figure 14:
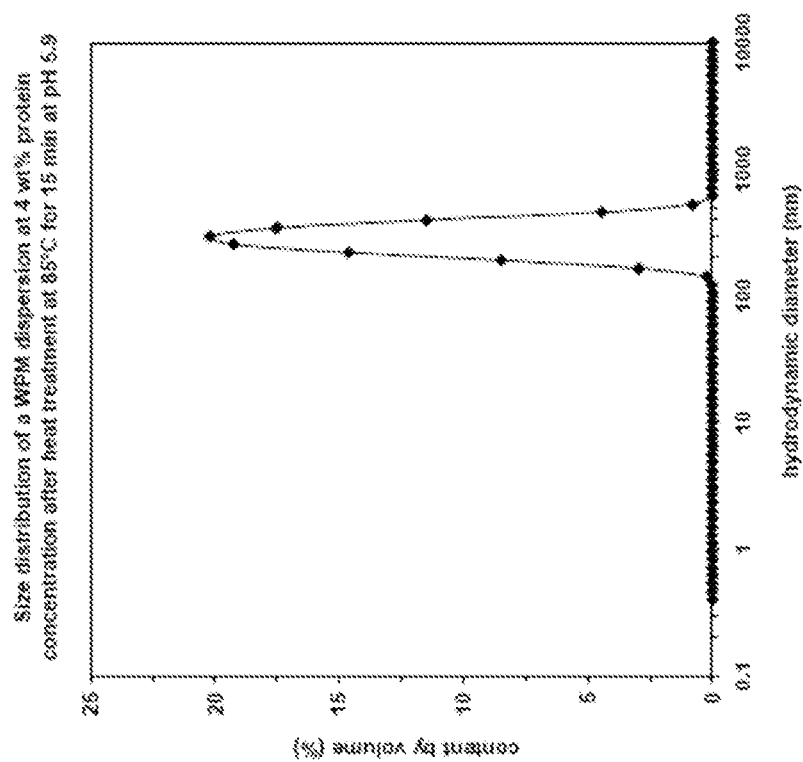

FIG. 14 is a graph showing the size distribution of micelles obtained by the process of the invention using a 4% Prolacta 90 whey protein isolate treated at pH 5.9.

Figure 15:
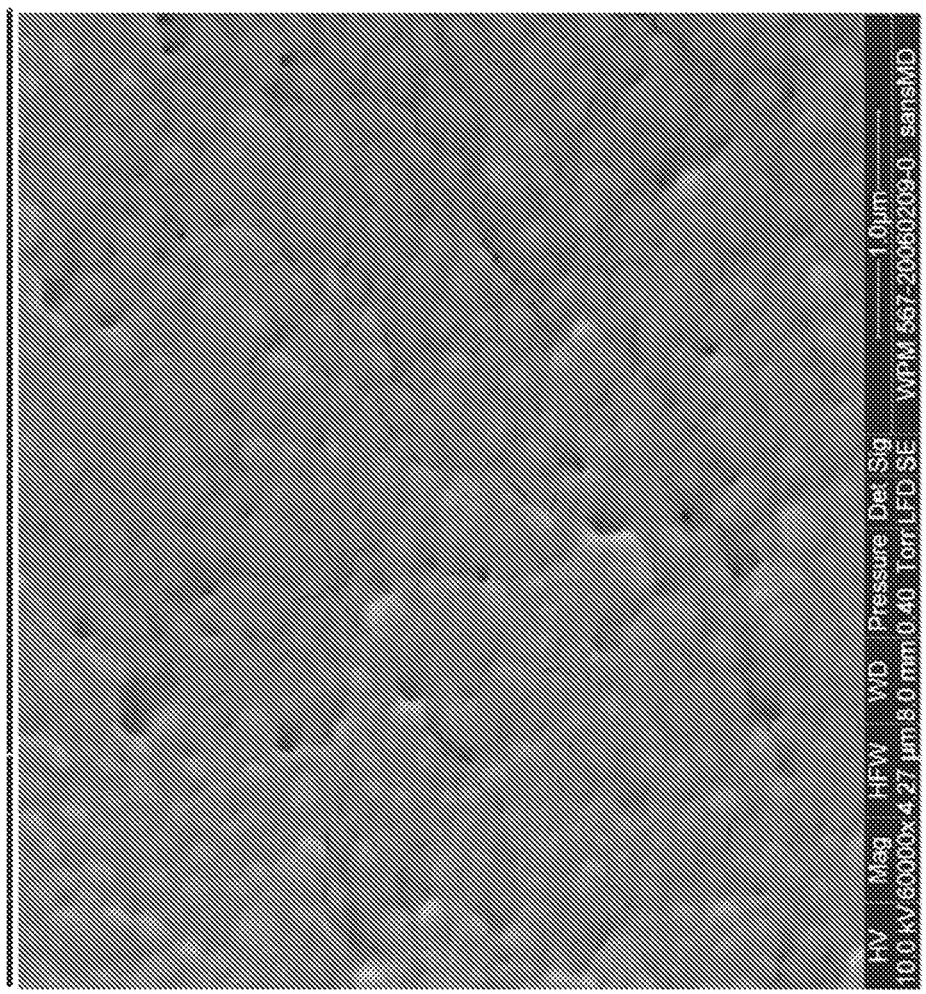

FIG. 15 is a SEM micrograph showing the internal structure after cutting of a spray-dried powder granule that is presented on FIG. 8.

Figure 16:
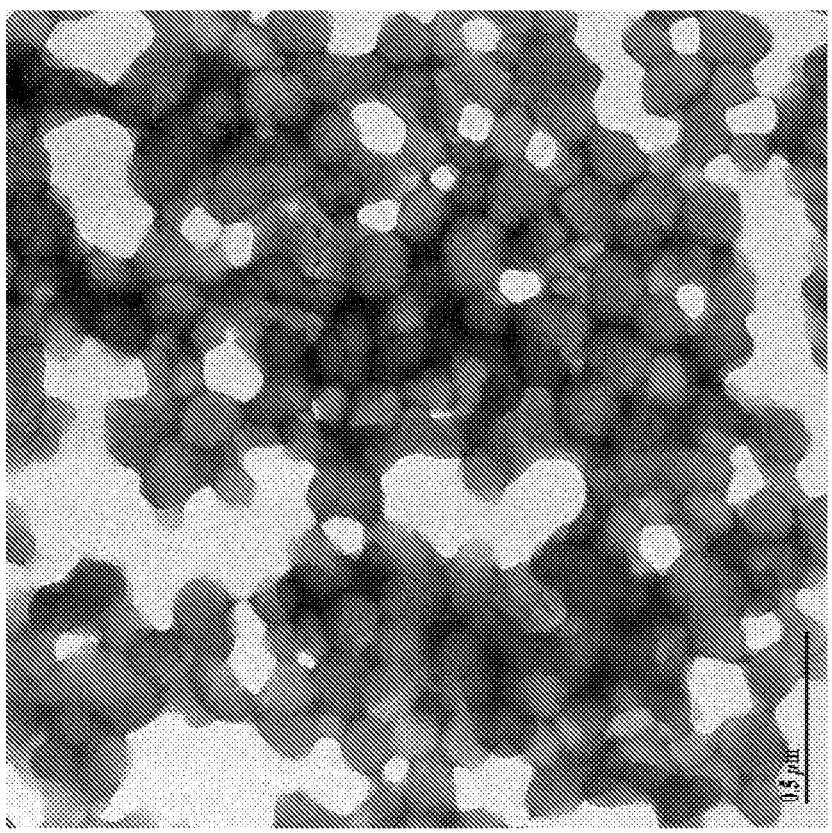

FIG. 16 is a negative staining TEM micrograph of a 4% whey protein micelles dispersion based on a pure freeze dried whey protein micelle powder after at room temperature in deionised water. Scale bar is 0.5 micrometre.

Figure 17:
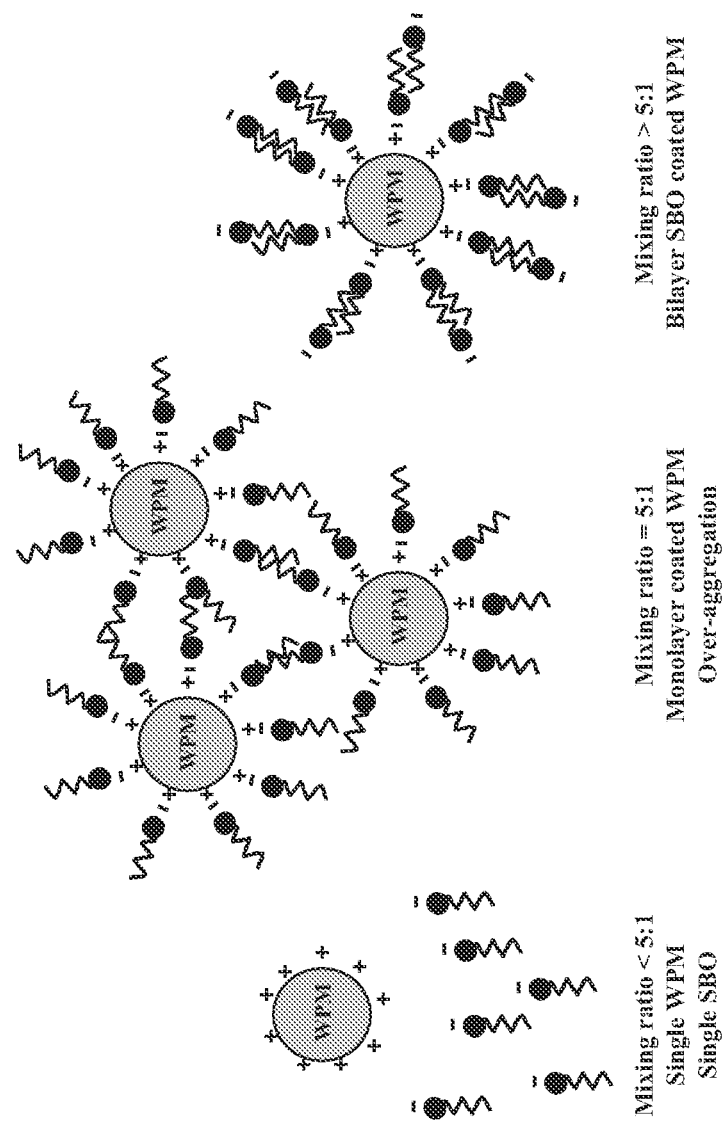

FIG. 17 is a schematic view of the WPM coating by SBO (sulphated butyl oleate) upon increasing the mixing ratio at pH 3.0. Grey circle: WPM with positive surface charges. Black head+tail: negatively charged head and hydrophobic tail from SBO.

Figure 18:

FIG. 18 is a photograph of a whey protein micelle concentrate at 20% obtained after evaporation in which 4% NaCl is added.

Figure 19:
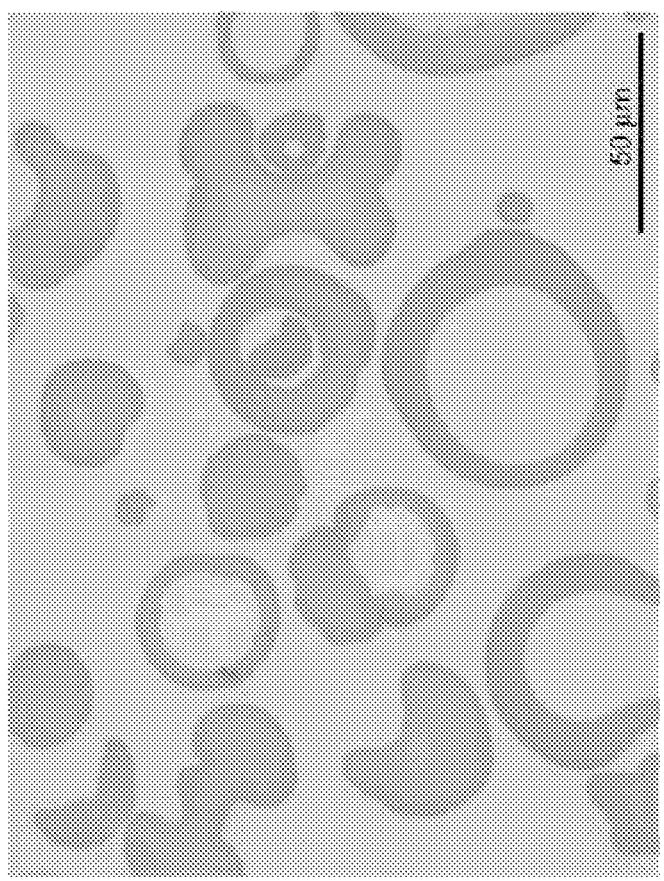

FIG. 19 is a bright field light microscopy micrograph of whey protein micelle powder semi-thin section after toluidine blue staining. Scale bar is 50 microns.

Figure 20:
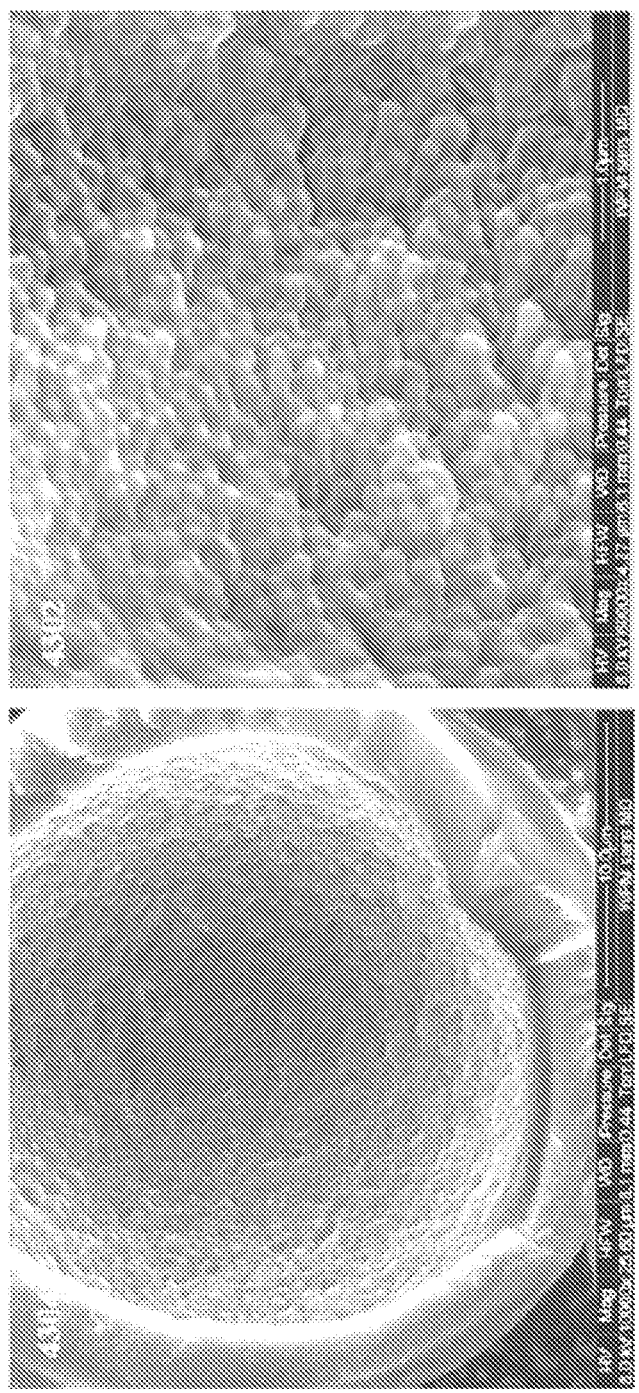

FIG. 20 is a SEM micrograph of the hollow whey protein micelle powder particle after cutting. Left: internal structure. Right: Detail of the whey protein micelle composing the powder particle matrix. Scale bars are 10 and 1 micron respectively.

DETAILED DESCRIPTION OF THE INVENTION

According to the present invention, a method for preparing aggregates of protein and active agent is provided, which aggregate may then constitute a delivery system in the field of nutrition and/or cosmetics. The aggregates of the present invention are the result of an association of whey protein micelles with an active agent.

The whey protein micelles used in the method of the present invention are schematically represented in FIG. 7, wherein the whey proteins are arranged in such a way that the hydrophilic parts of the proteins are oriented towards the outer part of the agglomerate and the hydrophobic parts of the proteins are oriented towards the inner "core" of the micelle. This energetically favourable configuration offers good stability to these structures in a hydrophilic environment.

The specific micelle structure can be seen from the figures, in particular FIGS. 3, 9, 10, 13 and 15, wherein the micelles used in the present invention consist essentially of spherical agglomerates of denatured whey protein. The micelles of the present invention are particularly characterised by their regular, spherical shape.

Due to their dual character (hydrophilic and hydrophobic), this denatured state of the protein seems to allow interaction with a hydrophobic phase, e.g. a fat droplet or air, and a hydrophilic phase. The whey protein micelles therefore have perfect emulsifying and foaming properties.

Furthermore, the micelles may be produced in such a way that they have an extremely sharp size distribution (see FIG. 14), such that more than 80% of the micelles produced will have a size smaller than 1 micron, preferably between 100 nm and 900 nm, more preferably between 100-770 nm, most preferably between 200 and 400 nm.

The mean diameter of the micelles can be determined using Transmission Electron Microscopy (TEM). In order to do so, the liquid micelle samples are encapsulated in agar gel tubes. Fixation is achieved by immersion in a solution of 2.5% glutaraldehyde in 0.1M, pH 7.4 cacodylate buffer and post-fixation with 2% Osmium tetroxide in the same buffer, both solutions containing 0.04% Ruthenium red. After dehydration in a graded ethanol series (70, 80, 90, 96, 100% ethanol), the samples are embedded in Spurr resin (Spurr/ethanol 1:1, 2:1, 100%). After polymerization of the resin (70° C., 48 hours), semi-thin and ultra-thin sections are cut with a Leica ultracut UCT ultra-microtome. Ultra-thin sections, stained with aqueous uranyl-acetate and lead citrate, are then examined by transmission electron microscopy (Philips CM12, 80 kV).

Without wishing to be bound by theory, it is thought that during micelle formation, the micelles reach a "maximum" size, due to the overall electrostatic charge of the micelles repelling any additional protein molecule, such that the micelles cannot grow in size any longer. This accounts for the narrow size distribution observed (cf. FIG. 14).

The micelles described above may be produced by a process which is described in detail in the following.

As the whey protein which may be used for the manufacture of whey protein micelles, any commercially available whey protein isolates or concentrates may be used, i.e. whey protein obtained by any process for the preparation of whey protein known in the art, as well as whey protein fractions prepared therefrom or proteins such as β-lactoglobulin (BLG), α-lactalbumin and serum albumin. In particular, sweet whey obtained as a by-product in cheese manufacture, acid whey obtained as by-product in acid casein manufacture, native whey obtained by milk microfiltration or rennet whey obtained as by-product in rennet casein manufacture may be used as the whey protein. The whey protein may be from a single source or from mixtures of any sources. It is preferable that the whey protein does not undergo any hydrolysis step prior to micelle formation. Thus, the whey protein is not subjected to any enzymatic treatment prior to micellisation. According to the invention, it is important that the whey protein be used in the micelle formation process and not hydrolysates thereof.

The whey protein source for the manufacture of micelles is not restricted to whey isolates from bovine origin, but pertains to whey isolates from all mammalian animal species, such as from sheep, goats, horses, and camels. Also, the manufacturing process applies to mineralised, demineralised or slightly mineralised whey preparations. By "slightly mineralized" is meant any whey preparation after elimination of free minerals which are dialyzable or diafiltrable, but which maintains minerals associated to it by natural mineralisation after preparation of the whey protein concentrate or isolate, for example. These "slightly mineralised" whey preparations have had no specific mineral enrichment.

Whey proteins are an excellent source of essential amino acids (AA) (45%). Compared to casein (containing 0.3 g cysteine/100 g protein), sweet whey proteins contain 7 times more cysteine, and acid whey 10 times more cysteine. Cysteine is the rate limiting amino acid for glutathione (GSH) synthesis, a tripeptide made of glutamate cysteine and glycine which has primary important functions in the defense of the body in case of stress. Requirements in these amino acids may be increased in case of stress and in elderly people. Also, glutathione oral supplementation with whey protein has been shown to increase plasma GSH levels of HIV-infected patients (Eur. J. Clin. Invest. 2001; 31, 171-178).

Other health benefits provided by whey proteins include enhancement of muscle development and building, as well as muscle maintenance in children, adults or elderly people, enhancement of the immune function, improvement of cognitive function, control of blood glucose such that they are suitable for diabetics, weight management and satiety, anti-inflammatory effects, wound healing and skin repair, lowering of the blood pressure, etc.

Whey proteins have a better protein efficiency ratio (PER=118) compared for example to casein (PER=100). PER is a measure of a protein quality assessed by determining how well such protein supports weight gain. It can be calculated by the following formula:

PER=body weight growth (g)/protein weight intake (g).

| Examples: | PER | % Casein |
|---|---|---|
| casein | 3.2 | 100 |
| Egg | 3.8 | 118 |
| Whey | 3.8 | 118 |
| Whole Soya | 2.5 | 78 |
| Wheat gluten | 0.3 | 9 |

For the micellisation process, whey proteins may be present in an aqueous solution in an amount of 0.1 wt. % to 12 wt. %, preferably in an amount of 0.1 wt. % to 8 wt. %, more preferably in an amount of 0.2 wt. % to 7 wt. %, even more preferably in an amount of 0.5 wt. % to 6 wt. %, most preferably in an amount of 1 wt. % to 4 wt. % on the basis of the total weight of the solution.

The aqueous solution of the whey protein preparation as present before the micellisation step may also comprise additional compounds, such as by-products of the respective whey production processes, other proteins, gums or carbohydrates. The solution may also contain other food ingredients (fat, carbohydrates, plant extracts, etc). The amount of such additional compounds preferably doesn't exceed 50 wt. %, preferably 20 wt. %, and more preferably does not exceed 10 wt. % of the total weight of the solution.

The whey protein, as well as the fractions and/or the main proteins thereof may be used in purified form or likewise in form of a crude product. Preferably, the content of divalent cations in the whey protein for the preparation of the whey protein micelles concentrate is less than 2.5%, more preferably less than 2%, even more preferably less than 0.2%. Most preferably the whey proteins are completely demineralised.

Figure 1:
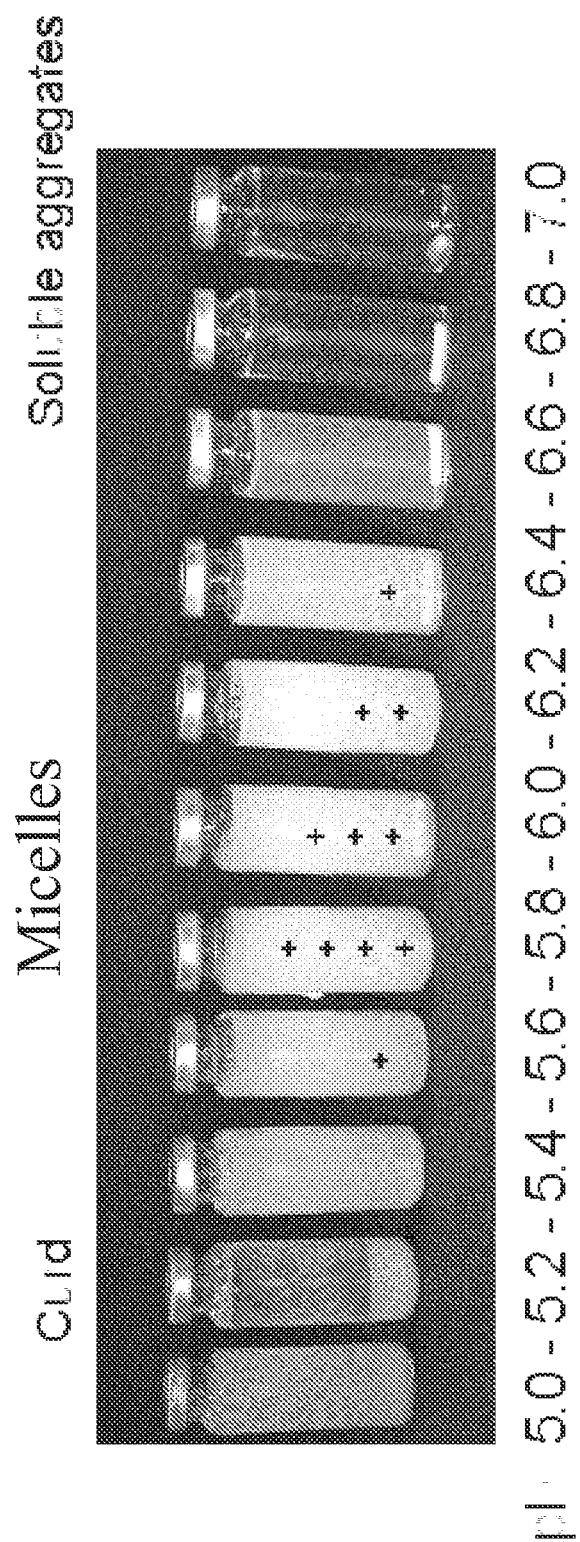
FIG. 1 shows the result of an experiment demonstrating the effect of pH and heat treatment on the micellisation of β-lactoglobulin.
Figure 6:
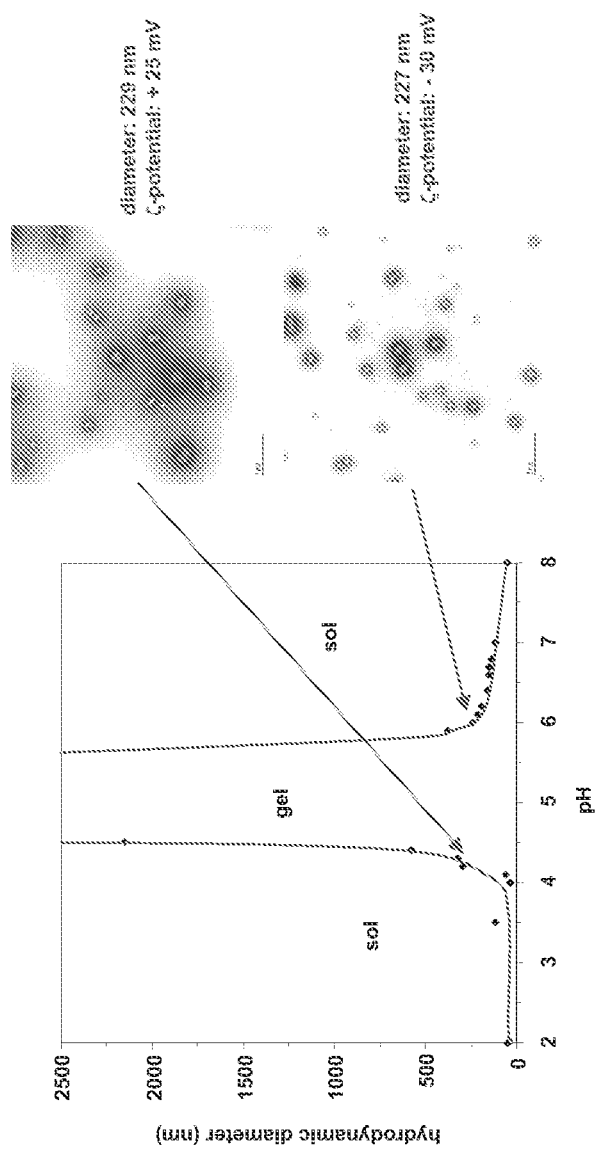
FIG. 6 shows the intensity-based equivalent hydrodynamic diameter of whey protein obtained by heat-treatment of a 1 wt % β-lactoglobulin dispersion for 15 min at 85° C. at pH ranging from 2 to 8.

PH and ionic strength are important factors in the micellisation of whey proteins. Thus, for extensively dialyzed samples which are virtually devoid or depleted of free cations such as Ca, K, Na, Mg, it has been found that when performing the heat treatment during a time period of 10 s to 2 hours at a pH below 5.4, curd is obtained, while at a pH exceeding 6.8, soluble whey protein results (see FIG. 1). Thus, only in this rather narrow pH window will whey proteins micelles having a diameter of less than 1 µm be obtained. These micelles will have an overall negative charge. The same micelle form can also be obtained symmetrically below the isoelectrical pH, i.e from 3.5 to 5.0, more preferably 3.8 to 4.5, resulting in micelles being positively charged (see FIG. 6).

Thus, in order to obtain positively charged micelles, micellisation of whey proteins may be done in a salt free solution at a pH value adjusted between 3.8 and 4.5 depending on the mineral content of the protein source.

Preferably, the micelles obtained will have an overall negative charge. Thus, the pH is adjusted to a range of from 6.3 to 9.0, for a content in divalent cations comprised between 0.2% and 2.5% in whey protein powder.

More specifically, to obtain negatively charged micelles, the pH is adjusted to a range of from 5.6 to 6.4, more preferably from 5.8 to 6.0 for a low divalent cation content (e.g. less than 0.2% of the initial whey protein powder). The pH may be increased up to 8.4 depending on the mineral content of whey protein source (concentrate or isolate). In particular, the pH may be between 7.5 to 8.4, preferably 7.6 to 8.0 to obtain negatively charged micelles in the presence of large amounts of free minerals and the pH may be between 6.4 to 7.4, preferably 6.6 to 7.2 to obtain negatively charged micelles in the presence of moderate amounts of free minerals. As a general rule, the higher the calcium and/or magnesium content of the initial whey protein powder, the higher the pH of micellisation.

In order to standardize the conditions of formation of the whey protein micelles, it may be most preferable to demineralise by any of the known demineralisation techniques (dialysis, ultrafiltration, reverse osmosis, ion exchange chromatography . . . ), any source of liquid native whey proteins with a protein concentration ranging from that of sweet whey, microfiltration permeate of milk or acid whey (0.9% protein content) to that of a concentrate at 30% protein content. The dialysis can be done against water (distilled, deionised or soft), but as this will only allow removal of the ions weakly bound to the whey proteins, it is more preferable to dialyse against an acid at pH below 4.0 (organic or inorganic) to better control the ionic composition of the whey proteins. By doing so, the pH of whey protein micelle formation will be below pH 7.0, more preferably comprised between 5.8 to 6.6.

Prior to heating the whey protein aqueous solution, the pH is generally adjusted by the addition of acid, which is preferably food grade, such as e.g. hydrochloric acid, phosphoric acid, acetic acid, citric acid, gluconic acid or lactic acid. When the mineral content is high, the pH is generally adjusted by the addition of alkaline solution, which is preferably food grade, such as sodium hydroxide, potassium hydroxide or ammonium hydroxide.

Figure 4:
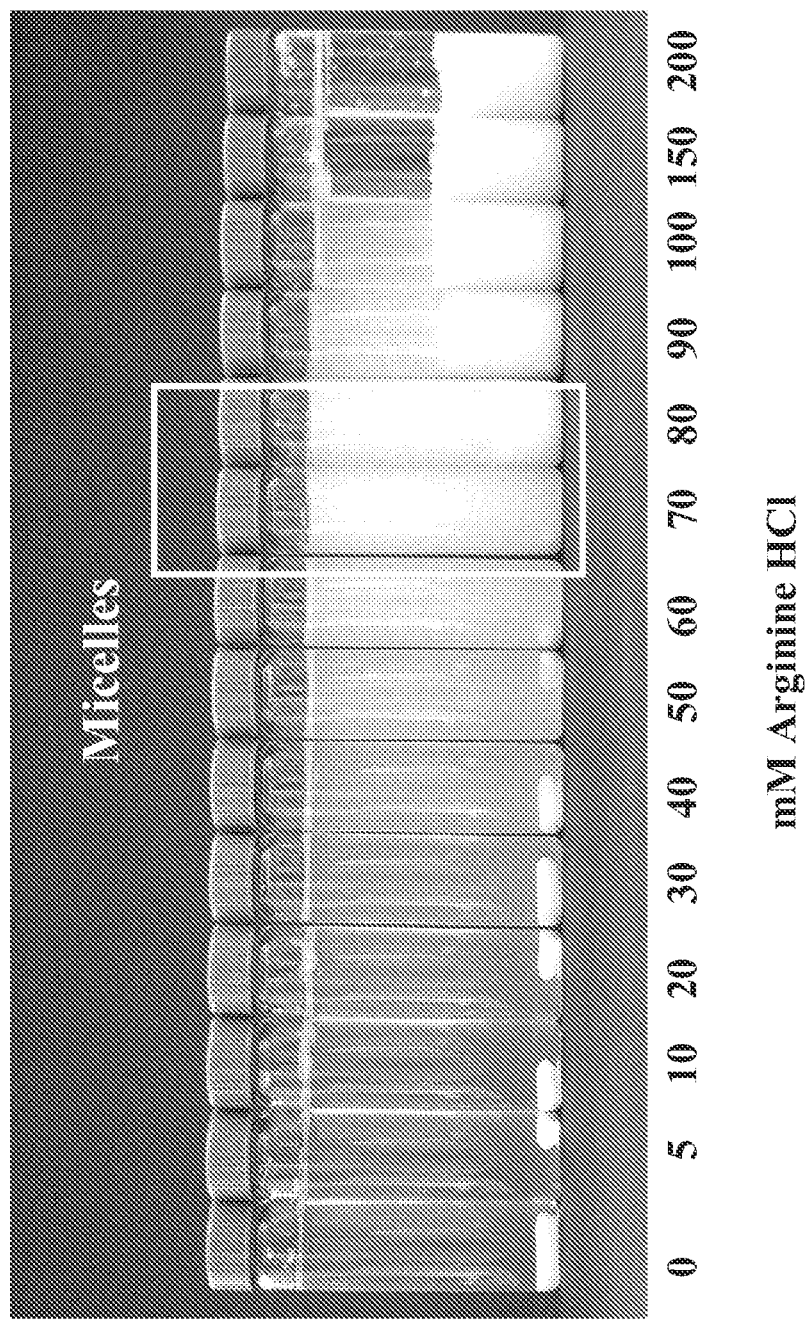
FIG. 4 shows the result of an experiment evaluating the impact of the ionic strength (Arginine HCl) on the formation of protein micelles at constant pH of 7.0.

Alternatively, if no pH adjustment step is desired, it is possible to adjust the ionic strength of the whey protein preparation while keeping the pH constant. Then, ionic strength may be adjusted by organic or inorganic ions in such a way that allows micellisation at a constant pH value of 7. FIG. 4 shows that micelles may be formed at a constant pH value of 7.0 while the ionic strength is varied by the addition of 70-80 mM of arginine HCl.

A buffer may be further added to the aqueous solution of whey protein so as to avoid a substantial change of the pH value during heat treatment of the whey protein. In principle, the buffer may be selected from any food-grade buffer system, i.e. acetic acid and its salts, such as e.g. sodium acetate or potassium acetate, phosphoric acid and salts thereof, e.g. $NaH_2PO_4$, $Na_2HPO_4$, $KH_2PO_4$, $K_2HPO_4$, or citric acid and salts thereof etc.

Adjusting the pH and/or the ionic strength of the aqueous solution results in a controlled process yielding micelles having a size between 100 nm-900 nm, preferably between 100-700 nm, most preferably between 200-400 nm. Preferably, the distribution of micelles having dimensions between 100-700 nm is greater than 80% when carrying out the process of micellisation described herein (see FIG. 14).

It is preferable that the whey protein does not undergo any hydrolysis step prior to micelle formation. Thus, the whey protein is not subjected to any enzymatic treatment prior to micellisation. According to the invention, it is important that the whey protein be used in the micelle formation process and not hydrolysates thereof.

In a second step, the starting whey protein aqueous solution is then subjected to heat treatment. In this respect it has been found that for obtaining whey protein micelles, it is important to have the temperature in the range of from about 70 to below 95° C., preferably of from about 82 to about 89° C., more preferably of from about 84 to about 87° C., most preferred at about 85° C. It has also been found that, on an industrial scale, it is important that the temperature be preferably less than 95° C., more preferably between 80° C. and 90° C., most preferably about 85° C.

Once the desired temperature has been reached, the starting whey protein aqueous solution is kept at this temperature for a minimum of 10 seconds and a maximum of 2 hours. Preferably, the time period during which the aqueous whey protein solution is kept at the desired temperature ranges from 12 to 25 minutes, more preferably from 12 to 20 minutes, or most preferably about 15 minutes.

The heat treatment may also be achieved in a microwave oven or any similar equipment allowing heating by microwaves with a time/quantity ratio of 10 s/10 mL for a 4 wt % protein solution heated in a 1500 W apparatus up to boiling temperature (98° C. at an altitude of 833 m). A continuous process may also be used by addition of 8 or more magnetrons around a glass tube potentially prolonged by a holding tube to increase the time of incubation.

Figure 2:
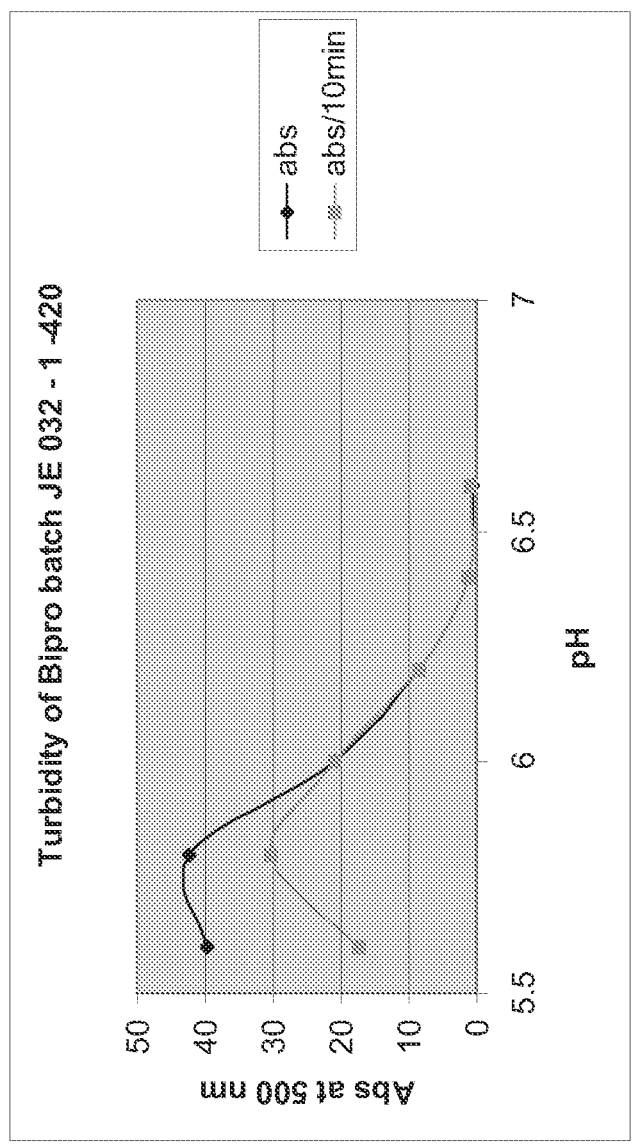
FIG. 2 is showing a mean to determine the pH of micellisation for a commercial preparation (Bipro®, Batch JE032-1-420) using turbidity measurements at 500 nm.

As shown in FIG. 2, turbidity measurements are an indication of micelle formation. The turbidity measured by absorbance at 500 nm may be at least 3 absorbance units for 1% protein solution but can reach 16 absorbance units when the yield of micellisation is above 80% (see FIG. 2).

To further illustrate the effect of micelle formation from a physicochemical point of view, a 1 wt % dispersion of Bipro® was heated for 15 minutes at 85° C. at pH 6.0 and 6.8 in MilliQ water. The hydrodynamic diameter of the aggregates obtained after heat treatment was measured by dynamic light scattering. The apparent molecular weight of the aggregates was determined by static light scattering using the so-called Debye plot. The surface hydrophobicity was probed using the hydrophobic ANS probe and the free accessible thiol groups by the DTNB method using cystein as the standard amino acid. Finally, the morphology of the aggregates was studied by negative staining TEM. The results are presented in table 1.

TABLE 1

Physicochemical properties of soluble whey protein aggregates obtained by heat treatment (85° C., 15 min) of a 1 wt % protein dispersion in presence or absence of NaCl.

| pH | hydrodynamic diameter (nm) | molecular weight $M_w$ ($\times 10^6$ g·mol$^{-1}$) | morphology | ζ-potential (mV) | protein surface hydrophobicity (μg·mmol$^{-1}$ ANS) | accessible SH groups (nmol SH·mg$^{-1}$ prot.) |
|---|---|---|---|---|---|---|
| 6.0 | 120.3 ± 9.1 | 27.02 ± 8.09 | Spherical micelles | −31.8 ± 0.8 | 105.4 | 3.5 ± 0.4 |
| 6.8 | 56.2 ± 4.6 | 0.64 ± 0.01 | linear aggregates | −27.9 ± 1.2 | 200.8 | 6.8 ± 0.5 |

From table 1, it is clear that the whey protein micelles that were formed at pH 6.0 allow protein to decrease its specific ANS surface hydrophobicity by a factor of 2 compared to non-micellised whey protein heated in the same condition, but at pH 6.8. The micelle formation can be also seen on the very high molecular weight of 27×10$^6$ g.mol$^{-1}$ compared to 0.64×10$^6$ g.mol$^{-1}$ for non-micellised protein, indicating a very condensed state of the matter within the micelle (low amount of water). Interestingly enough, the ζ-potential of the micelles is even more negative than the non-micellised proteins even if the latter have been formed at a more basic pH than the micelles. This is the result of a more hydrophilic surface of the micelles being exposed to the solvent. Finally, one should note that the thiol reactivity of the micelles is much lower than that of the non-micellised protein because of the different pH of heat treatment.

It has been found that the conversion yield of native whey protein to micelles decreases when the initial protein concentration is increased before pH adjustment and heat treatment. For example, when starting with a whey protein isolate Prolacta 90 (lot 673 from Lactalis), the yield of formation of whey protein micelles drops from 85% (when starting with 4% proteins) to 50% (when starting with 12% of proteins). In order to maximize the formation of whey protein micelles (>85% of the initial protein content), it is better to start with an aqueous whey protein solution having a protein concentration below 12%, preferably below 4%. Depending on the intended final applications, the protein concentration is adjusted before heat treatment to manage the optimal whey protein micelles yield.

The whey proteins micelles obtainable according to the process described above shall have a size with a diameter of less than 1am, preferably of from 100 to 990 nm, more preferably from 100 to 700 nm, most preferably from 200-400 nm.

Depending on the desired application, the yield of micelles is of at least 50%, preferably at least 80% and the residual soluble aggregates or soluble protein content is preferably below 20%. The average micelle size is characterised by a polydispersity index below 0.200. It has been observed that whey protein micelles could form aggregates around pH 4.5, with however no sign of macroscopic phase separation after at least 12 hours at 4° C.

The purity of whey protein micelles which may be produced according to the process described herein can be obtained by determining the amount of residual soluble proteins. Micelles are eliminated by centrifugation at 20° C. and 26900 g for 15 min. The supernatant is used to determine the protein amount in quartz cuvettes at 280 nm (1 cm light pathlength). Values are expressed as a percentage of the initial value before heat treatment.

Proportion of micelles=(Amount of initial proteins–amount of soluble proteins)/Amount of initial proteins The whey protein micelles obtainable according to a process described herein have not been submitted to any mechanical stress leading to reduction of the particle size during formation. The process induces spontaneous micellisation of whey proteins during heat treatment in the absence of shearing.

Whey protein micelles used in the present invention may be produced according to the micellisation process described above but are not limited thereto.

According to an embodiment of the present invention, the whole micellisation process described above may be carried out on a dispersion of native whey protein and active agent, such that upon micelle formation, an aggregate of whey protein micelle and active agent is produced.

Thus the method comprises the steps of dispersing native whey protein and an active agent in an aqueous solution, and denaturing the whey protein to whey protein micelles and forming an aggregate of whey protein micelles and the active agent. Micellisation may be carried out according to a process described above. Preferably, micellisation is carried out by adjusting the pH of the native protein aqueous solution to a range between 5 and 8 and heating said solution at a temperature between 80° C. and 95° C., preferably below 95° C., more preferably between 80° C. and 90° C., most preferably about 85° C., for at least 10 s.

Accordingly, the amount of active agent present in the dispersion prior to micellisation is between 0.1% and 50%.

According to another method of the present invention, the active agent is dispersed in a solvent with whey protein micelles. The whey protein micelles may be used as such or may be used in the form of concentrates and/or powders thereof. Additionally, the whey protein micelles may be coated with an emulsifier such as phospholipids, for example, other coating agents such as a protein, a peptide, a protein hydrolysate or a gum such as acacia gum in order to modulate the functionality of the whey protein micelles. When a protein is used as a coating agent, it may be selected from any proteins having an isoelectric point significantly higher or lower than whey protein. These are, for example, protamine, lactoferrin and some rice proteins. When a protein hydrolysate is used as coating agent, it is preferably a hydrolysate from proteins such as protamine, lactoferrin, rice, casein, whey, wheat, soy protein or mixtures thereof. Preferably, the coating is an emulsifier selected from sulphated butyl oleate, diacetyltartaric acid esters of mono- and diglycerides, citric acid esters of monoglycerides, stearoyl lactylates and mixtures thereof. FIG. 17 is a schematic representation of such coating with sulphated butyl oleate. Furthermore, co-spraydrying, as described further herein, may also result in a coating of the whey protein micelles.

Micelles concentrates may be produced by evaporation, centrifugation, sedimentation, ultrafiltration and/or microfiltration, for example.

Evaporation may be carried out on the micelles by feeding the micelle suspension obtained after heat treatment to an evaporator under vacuum, having a temperature between 50° C. and 85° C. The whey protein micelles concentrate obtained by evaporation tend to have a creamy, semi-solid texture (as shown in FIG. 18) which may be used in the methods of the present invention.

Centrifugation may be carried out with high acceleration rate (more than 2000 g) or low acceleration rate (less than 500 g) after acidification of the whey protein micelle dispersion at a pH lower than 5, preferably 4.5.

Spontaneous sedimentation may also be carried out on the whey protein micelle dispersion by acidification. Preferably, the pH will be 4.5 and the sedimentation time is more than 12 hours.

Alternatively, concentration of the whey protein micelles may be achieved by microfiltration of the micelles suspension obtained after heat treatment. This enriching technique not only enables to concentrate whey protein micelles by removing the solvent but also enables the removal of non-micellised protein (such as native proteins or soluble aggregates). Thus, the final product only consists of micelles (as can be checked by Transmission Electron Microscopy—cf. FIGS. 9 and 10). In this case, the concentration factor that is possible to achieve is obtained after the initial flow rate of permeate through the membrane has dropped to 20% of its initial value.

The whey protein concentrate obtained by microfiltration may have a protein concentration of at least 12%. Furthermore, the concentrate may contain at least 50%, preferably at least 80% of the protein in the form of micelles.

It is interesting to note that the concentrate, if adjusted to a protein content of 10% has the ability to withstand a subsequent heat treatment at 85° C. for 15 min at pH 7.0 in presence for example of up to 0.15 M of sodium chloride, as shown in FIG. 11. As a matter of comparison, a native whey protein dispersion (Prolacta90, lot 500658 from Lactalis) forms a gel in the presence of 0.1 M of sodium chloride at a protein concentration of only 4% (cf. FIG. 12). This confirms the high stability to external factors of the whey protein micelles used in the present invention.

In the present invention, the micelles may be provided as whey protein micelles or as whey protein micelles concentrate in liquid form as a dispersion, in semi-solid form, or in a dried form. The whey protein micelles concentrate may be used as such or diluted depending on the application.

A dried form of micelles may be obtained by any known techniques, such as spray-drying, freeze-drying, roller drying etc, which may be carried out on the whey protein micelles or concentrates thereof. Accordingly, drying may be carried out with or without addition of further ingredients.

FIG. 8 shows a powder obtained by spray-drying without addition of any further ingredients, having an average particle diameter size greater than 1 micron due to the micelle aggregation occurring during spray-drying. A typical average volume median diameter ($D_{43}$) of such powders is between 45 and 55 microns, preferably 51 microns. The surface median diameter ($D_{32}$) of such powders is preferably between 3 and 4 microns, more preferably it is 3.8 microns.

The moisture content of the powders obtained after spray-drying is preferably less than 10%, more preferably less than 4%.

Whey protein micelle powders may be used in the present invention. Preferably, these powders will be "pure". By "pure powder" is meant a powder comprising at least 90% whey protein. Said whey protein micelles powder is characterised by a very high flowability. These powders behave almost as liquids and present the advantages of easy usability and transferability. The angle of repose of these powders is preferably below 35°, more preferably below 30°. Such a low angle of repose allows the powders to be used as flowing agents in cosmetic applications or food applications, for instance.

Furthermore, the whey protein micelles powder have a high binding capacity for solvents such as water, glycerol, ethanol, oil, organic solvents etc. The binding capacity of the powders to oil is at least 30%, to water is at least 50%, preferably at least 90%, most preferably at least 100%. For solvents such as glycerol and ethanol, the binding capacity is of at least 50%. This property of the whey protein micelle powders allows these to be sprayed or filled with further active agents selected from the group of peptides, plant extracts, protein hydrolysates, bioactives, vitamins, minerals, pharmaceuticals, cosmetic components etc. and mixtures thereof. The complex formed may then act as a delivery agent according to the present invention.

A important feature of whey protein micelles is that basic micelle structure of the whey proteins is conserved upon processing or reconstitution in solvents. FIG. 15 shows a whey protein micelle powder grain which has been sectioned, and whereby the individual whey protein micelles are observable. Furthermore, the micelle structure can be easily reconstituted in solvents. It has been shown that the powders obtained from whey protein micelle concentrate can be easily redispersed in water at room temperature or at 50° C. The size and structure of the whey protein micelles are fully conserved compared to the initial concentrate. For example, in FIG. 13, the whey protein concentrate that was spray-dried at 20% protein concentration has been redispersed in deionised water at 50° C. at a protein concentration of 50%. The structure of the micelles has been probed by TEM and can be compared to FIG. 10. A similar shape of micelles was obtained. The diameter of the micelles was found to be 315 nm by dynamic light scattering with a polydispersity index of 0.2. FIG. 16 also shows dispersion of a freeze-dried whey protein micelle powder, wherein the micelles are reconstituted.

For carrying out the method of the present invention, whey protein micelles, concentrates thereof or powders thereof in any form may be used. These may be in a suspension, in a semi-solid form, or in a dried form. Thus, in a first step a dispersion comprising whey protein micelles and an active agent in a solvent is formed. The solvent may be any solvent. For instance, it may be water, organic solvents, ethanol, glycerol, oils etc.

Active agents may be any agent selected from vitamins, minerals, antioxidants, poly-unsaturated fatty acids, peptides, plant extracts, protein hydrolysates, bioactives, aroma, sweeteners, sugars, polysaccharides, sucrose, supplements, pharmaceuticals, drugs, cosmetic components, components sensitive to heat, UV radiation, light, oxygen, metals, humidity, temperature etc. They may be unstable compounds such as polyphenols (from coffee, green tea etc.), lycopene and other carotenoids. They may include compounds such as caffeine, hesperidins, soluble or non-soluble salts, probiotic bacteria, stains, maltodextrins, fats, emulsifiers, ligands.

The active agents may also be minerals such as $Mg^{2+}$, $Fe^{2+}$, $Mn^{2+}$ etc. which are control released upon consumption of the food product, and/or application of the pharmaceutical or cosmetic composition.

The active agent may be provided as a single active agent or as a mixtures of active agents. It may be provided in an amount of 0.1% to 50% of the total weight of the aggregate.

Active agents may be in a dry form which is added to the dispersion of whey protein micelles in a solvent.

Alternatively, the active agent may be in a liquid form which may be sprayed directly onto the whey protein micelles. The liquid form may be the actual form of the active agent, or it may result from the dissolution or suspension of the active agent in a liquid. Said liquid may be the same as the solvent in which the whey protein micelles and the active agent are dispersed according to the method of the present invention. It may also be different.

Alternatively, the active agent in liquid form may be mixed with a whey protein micelle powder.

Evaporation of the dispersion solvent to yield the aggregates is then carried out. This may be done by any evaporation treatment known in the art. According to an embodiment, evaporation may be carried out by spray-drying such that the aggregates after spray-drying are in the form of a mixed powder comprising the whey protein micelles aggregated with the active agent. The resulting mixed whey protein micelle aggregates comprise whey protein micelles and active agents in a weight ratio ranging from 1:1 to 1:1000.

This co-spraydrying results in powders consisting of whey protein micelles agglomerated or coated with an additional ingredient.

The whey protein micelle powders obtained by the present invention are characterised by an internal structure composed mainly of hollow spheres but also of collapsed spheres (cf. FIG. 19). The hollow spheres structure can be easily explained by the formation of the vapour droplet within the WPM concentrate droplet during the spray drying. As the vapour droplet left the WPM droplet due to a temperature above 100° C., a hollow sphere remained. The "bone-shape" is due to a combination of the water evaporation from droplet and the external pressure within the droplet.

The internal structure of the spherical hollow spheres was investigated by SEM after sectioning the particle close to its diameter (FIG. 20, left). The wall thickness of the particle was around 5 µm and seemed very smooth, whereas the inner structure had a more grainy appearance. Increased magnification showed that this graininess was in fact due to the presence of the initial WPM that were fused to form the inner matrix of the powder particle. Interestingly, the spherical shape of the micelles was kept during spray drying as well the homogeneous particle size distribution (FIG. 20, right).

Thus, on a microscopic basis, whey protein micelle powders are characterised by a unique granule morphology of hollow or collapsed spheres containing intact and individualised whey protein micelles.

Evaporation may be avoided when using whey protein micelle powder, due to the capability of these powders to absorb the solvent to a certain extent while remaining in the powder form. Accordingly, a method of preparing whey protein micelle and active agent aggregates, whereby the active agent is mixed with a whey protein micelle powder is provided. Preferably, the powder will comprise at least 50% whey protein micelles.

The whey protein micelles powder have a high binding capacity for solvents such as water, organic solvents, glycerol, ethanol, oils etc. The binding capacity of the whey protein micelles powders to oil is at least 30%, to water is at least 50%, preferably at least 90%, most preferably at least 100%. For solvents such as glycerol and ethanol, the binding capacity is of at least 50%.

This presents the advantage that the active agent may be added to the whey protein micelle powder in a liquid form by mixing, spraying etc., and that the resulting aggregates are in the form of a powder, without further processing required.

The active agent may be included in the whey protein micelle powder in an amount of 0.1-50%, preferably 2-20%. Thus, the powder may act as a delivery vehicle for those active agents.

Due to their dual hydrophobic and hydrophilic character, whey protein micelles are able to absorb hydrophobic as well as hydrophilic compounds and solvents.

The aggregates of the present invention are such that they comprise at least one active agent associated with the whey protein micelles. These may be in the form of a whey protein matrix with at least one incorporated active agent. Said whey protein matrix may be in the form of an amorphous polymer.

The present invention thus provides a complex for delivery of active agent comprising whey protein micelles and said active agents.

The aggregates may be used in applications where slow release of active ingredients is desired. The whey protein micelles indeed present the advantage that a controlled release of the active agent is possible. Furthermore, the whey protein micelles may act as a versatile delivery vehicle which may improve the bioavailability of active agents. The micelles may indeed act as a lipid delivery vehicle for liposoluble vitamins, antioxidants, long-chain polyunsaturated fatty acids. Furthermore, on the one hand, they allow stabilisation of water soluble compounds such as catechins, polyphenols etc. by releasing liposoluble antioxidants. On the other hand, they may also stabilise liposoluble compounds such as long-chain polyunsaturated fatty acids, vitamin E etc. by releasing water soluble antioxidants. This versatility presents a great advantage over the delivery systems already known.

Further advantages offered by the aggregates of the present invention include their ability to modulate taste perception. For instance, caffeine bitterness perception is reduced when caffeine as an active agent is associated to the whey protein micelle according to the present invention and used in caffeinated nutrition bars, for instance. On the other hand, these aggregates may provide a saltiness/sweetness perception increase.

Furthermore, due to the presence of whey protein micelles, the aggregates of the present invention are also ideally suited for use as an emulsifier, fat substitute, substitute for micellar casein or foaming agent, since they are able to stabilize fat and/or air in an aqueous system for prolonged period.

Figure 5:
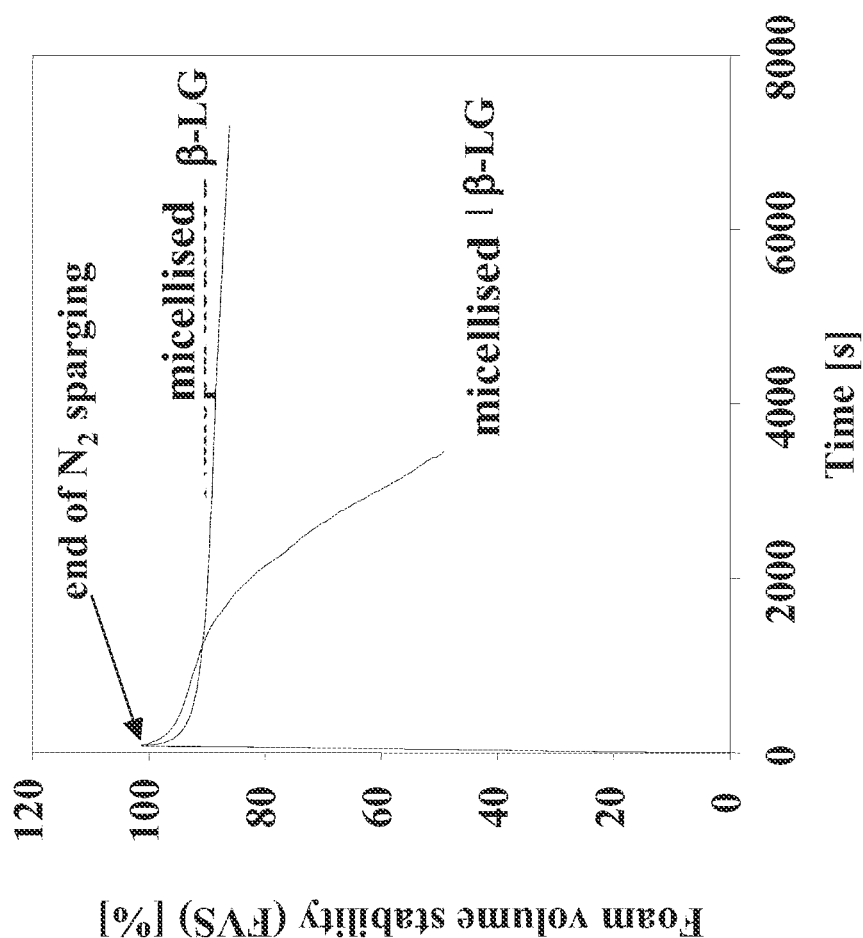
FIG. 5 shows the volume stability (FVS) of foam stabilized by 1 wt. % β-lactoglobulin micelles (Davisco) at pH 7.0 in presence of 60 mM Arginine HCl compared to non-micellised β-lactoglobulin.

The foam stability is shown in FIG. 5 which compares the use of non-micellised whey protein versus the micellised whey protein of the present invention.

Thus, the aggregates of the present invention may be used as an emulsifying agent, for which the material is ideally suited, since it has a neutral taste and no off-flavour is created by the use of such material. They may also be used as micellar casein substitute.

In addition, the present aggregates are still in a condition to serve as whitening agent, so that with one compound several tasks may be fulfilled. Since whey is a material abundantly available, the use thereof reduces the cost of a product requiring an emulsifying, filling, whitening or foaming agent. When used in nutritional applications, the aggregates therefore also contribute to the nutritional value of the food to which they are added.

Furthermore, whey protein micelle aggregates have a Protein Efficiency Ratio equivalent to the starting whey protein of at least 100, preferably at least 110, which makes them important nutritional ingredients.

Accordingly, the aggregates obtained according to any of the methods of the present invention can be used for the preparation of any kind of product requiring stabilisation of an emulsion or a foam, such as e.g. present in mousse or ice cream, in coffee creamers, or also in low fat or essentially fat free dairy products, or also where it finds application as a micellar casein substitute. In cosmetic applications, these may be used in foams, hair gels, body cream, ointments, shampoos etc.

Furthermore, the aggregates either alone or together with other materials, such as polysaccharides (e.g. acacia gum or carrageenans) may help to stabilize matrices and for example milky foam matrices. Due to their neutral taste, their whitening power and their stability, these aggregates may be used to increase skimmed milk whiteness and mouthfeel.

As well as increasing the whitening power of dairy systems for the same total protein content, the fat content in a food matrix may be reduced by using the aggregates of the present invention. Because whey protein micelles aggregates may be used as fat substitute while maintaining desirable structural, textural and organoleptic properties, a wider variety of low-fat product may be obtained.

The present invention thus provides a system, whereby all the advantages described above are provided while further offering the provision and delivery of active agents. This combination of effects presents a tremendous advantage over the delivery systems known in the art. Furthermore, the delivery system of the present invention may be used in the field of nutrition, pharmaceutics and cosmetics.

As a result, the aggregates of the present invention may be used in a wide range of applications. For instance, protein-enriched consumables containing active agents, such as chocolate, performance nutrition bars, dehydrated culinary products, chewing-gum etc. can be easily produced by using the whey protein micelle aggregates.

Furthermore, the aggregates of the present invention may be comprised in any kind of food product and/or cosmetic and/or pharmaceutical compositions such as for example, dairy products, mayonnaise, salad dressing, pasteurized UHT milk, sweet condensed milk, yoghurt, fermented milks, sauces, reduced fat sauces such as béchamel sauce for instance, milk-based fermented products, milk chocolate, mousses, foams, emulsions, ice creams, fermented cereal based products, milk based powders, instant food/drink powders, infant formula, diet fortifications, pet food, tablets, syrups, creams, ointments, sprays, body care, liquid bacterial suspensions, dried oral supplement, wet oral supplement etc.

Further applications include skin care and mouth care, such as toothpaste, chewing gum or gum-cleaning agent for instance.

In the present invention, any disclosure of list of ingredients is intended to disclose any possible combination of said ingredients, in any possible ratio.

The following examples illustrate the present invention without limiting it thereto.

EXAMPLES

The invention is further defined by reference to the following examples describing in detail the preparation of the micelles of the present invention. The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Example 1

Micellisation of β-Lactoglobulin

β-Lactoglobulin (lot JE002-8-922, 13-12-2000) was obtained from Davisco (Le Sueur, Minn., USA). The protein was purified from sweet whey by ultra-filtration and ion exchange chromatography. The composition of the powder is 89.7% protein, 8.85% moisture, 1.36% ash (0.079% $Ca^{2+}$, 0.013% $Mg^{2+}$, 0.097% $K^+$, 0.576% $Na^+$, 0.050% $Cl^-$). All other reagents used were of analytical grade (Merck Darmstadt, Germany).

The protein solution was prepared at 0.2% concentration by salvation of β-lactoglobulin in MilliQ® water (Millipore), and stirring at 20° C. for 2 h. Then pH of aliquots was adjusted to 5.0, 5.2, 5.4, 5.6, 5.8, 6.0, 6.2, 6.4, 6.6, 6.8, 7.0 by HCl addition. The solutions were filled in 20 ml glass vials (Agilent Technologies) and sealed with aluminum capsules containing a silicon/PTFE sealing. The solutions were heated at 85° C. for 15 min (time to reach the temperature 2.30-3.00 min). After the heat treatment, the samples were cooled in ice water to 20° C.

The visual aspect of products (FIG. 1) indicates that the optimal pH of micellisation is 5.8.

Example 2

Micellisation of Whey Protein Isolate

Whey protein isolate (WPI) (Bipro®, Batch JE032-1-420) was obtained from Davisco (Le Sueur, Minn., USA). The composition of the powder is reported in table 2.

The protein solution was prepared at 3.4% protein by solvation of whey protein powder in MilliQ® water (Millipore), and stirring at 20° C. for 2 h. The initial pH was 7.2. Then pH of aliquots was adjusted at 5.6, 5.8, 6.0, 6.2, 6.4 and 6.6 by HCl 0.1N addition.

The solutions were filled in 20 ml glass vials (Agilent Technologies) and sealed with aluminum capsules containing a silicon/PTFE sealing. The solutions were heated at 85° C. for 15 min (time to reach the temperature 2.30-2.50 min). After the heat treatment, samples were cooled in ice water to 20° C.

The turbidity of heated whey proteins has been determined at 500 nm and 25° C., samples were diluted to allow the measurement in the range of 0.1-3 Abs unit (Spectrophotometer Uvikon 810, Kontron Instrument). Values were calculated for the initial protein concentration 3.4%.

The pH of micellisation was considered to be reached upon stability (less than 5% variation of the initial value) of the absorbance measured at 500 nm within an interval of 10 minutes for the same sample as illustrated by the FIG. 2. For this product the optimal pH for micellisation was 6.0 to 6.2. For this pH adjusted before heat treatment stable turbidity was 21 and residual soluble protein evaluated by absorbance at 280 nm after centrifugation was 1.9%. We can conclude that 45% of initial proteins were transformed in micelles at pH 6.0.

TABLE 2

Composition of WPI and sample characteristics after micellisation

| | |
|---|---|
| Supplier | Davisco |
| Product name | Bipro |
| Batch number | JE 032-1-420 |
| Composition (mg/100 g) | |
| Sodium | 650 |
| Potassium | 44 |
| Chloride*10 if ≤ 40 | 10 |
| Calcium | 82 |
| Phosphorus | 49 |
| Magnesium | 6 |
| Initial pH | 7.2 |
| pH micellisation | 6.0 |
| Turbidity (500 nm) for 3.4% protein in solution | 21 |
| Residual Soluble protein (%) by absorbance at 280 nm | 1.9 |

Example 3

Microscopic Observation of Micelles

Production of Micelles:

Protein solution was prepared at 2% protein by salvation of whey protein powder (WPI 90 batch 989/2, Lactalis, Retier, France) in MilliQ® water (Millipore), and stirred at 20° C. for 2 h. Then pHs of aliquots were adjusted using HCl 0.1N or NaOH 0.1N.

The solutions were filled in 20 ml glass vials (Agilent Technologies) and sealed with aluminum capsules containing a silicon/PTFE sealing. The solutions were heated at 85° C. for 15 min (time to reach the temperature 2.30-2.50 min). After the heat treatment, the samples were cooled in ice water to 20° C. For this product the optimal pH for micellisation was 7.4.

Microscopic Observations:

Liquid micelle samples were encapsulated in agar gel tubes. Fixation was achieved by immersion in a solution of 2.5% glutaraldehyde in 0.1 M, pH 7.4 cacodylate buffer and post-fixation with 2% Osmium tetroxide in the same buffer, both solutions containing 0.04% Ruthenium red. After dehydration in a graded ethanol series (70, 80, 90, 96, 100% ethanol), the samples were embedded in Spurr resin (Spurr/ ethanol 1:1, 2:1, 100%). After polymerization of the resin (70° C., 48 hours), semi-thin and ultra-thin sections were cut with a Leica ultracut UCT ultra-microtome. Ultra-thin sections, stained with aqueous uranyl-acetate and lead citrate, were examined in transmission electron microscopy (Philips CM12, 80 kV).

Figure 3:
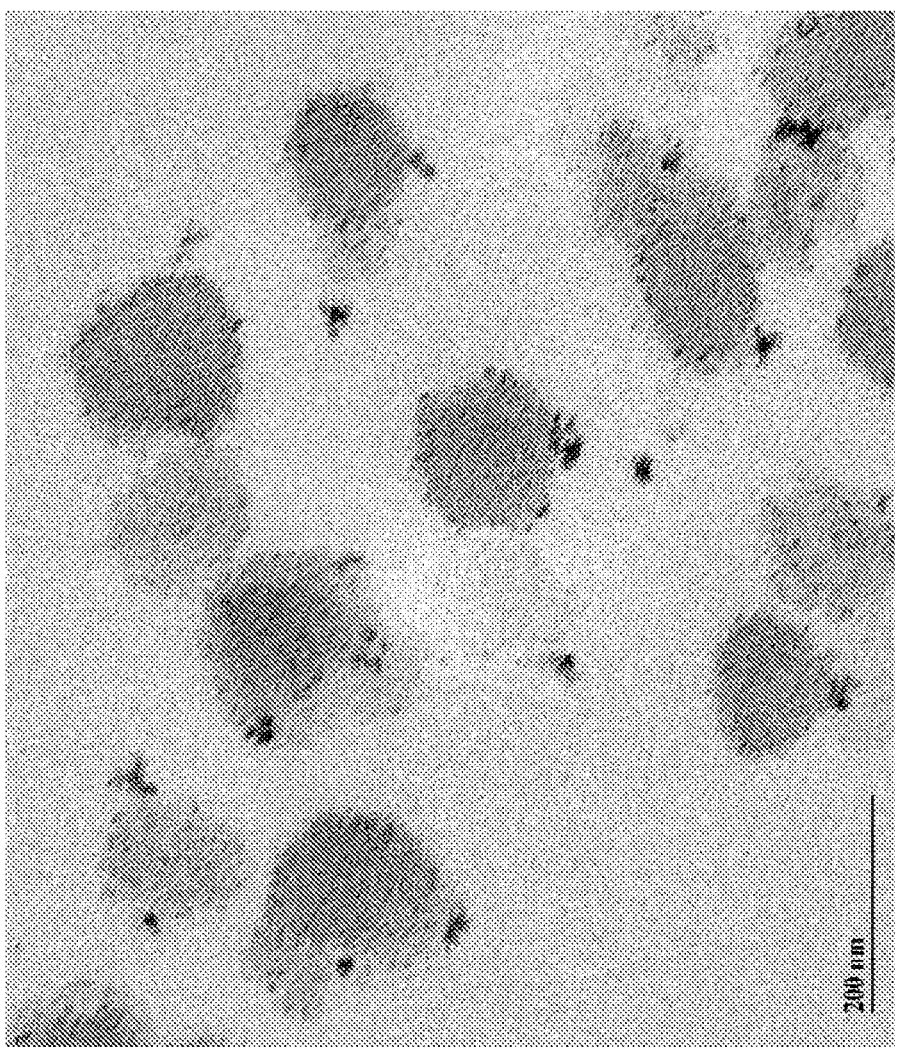
FIG. 3 is a Transmission Electron Microscopy micrograph from whey protein micelles (2 wt. %, WPI 95, Lactalis) at pH 7.4. Scale bar is 200 nm.

TEM micrograph is presented in FIG. 3. Obtained micelles are presenting a spherical shape with a diameter of 200 nm.

Particle Size Distribution

The intensity-based size distributions of micelles were measured for those micelles obtained by heat-treatment of a 1 wt % β-lactoglobulin dispersion for 15 min at 85° C. at pH 4.25 (positively charged with a zeta potential around +25 mV) and at pH 6.0 (negatively charged with a zeta potential around −30 mV). Z-averaged hydrodynamic diameter of the micelles was 229.3 mm at pH 4.25 an 227.2 at pH 6.0. β-LG and whey protein aggregations were followed using dynamic light scattering. A Nanosizer ZS apparatus (Malvern Instruments, UK)

equipped with a laser emitting at 633 nm and with 4.0 mW power was used. The instrument was used in the backscattering configuration, where detection is done at a scattering angle of 173°. This allows considerable reduction of the multiple scattering signals found in turbid samples. Samples were placed in a squared quartz cell (Hellma, pathlength 1 cm). The path length of the light beam was automatically set by the apparatus, depending on the sample turbidity (attenuation). The autocorrelation function was calculated from the fluctuation of the scattered intensity). The results are presented in FIG. 6. It shows that the average particle is characterized by a very narrow polydispersity index (<0.200).

Example 4

Micellisation of a β-lactoglobulin at a Constant pH

The method described in example 1 was repeated with the proviso of using an aqueous solution of 2% δ-lactoglobulin. The pH of this solution has been adjusted to 7.0 after adding Arginine HCl solutions to obtain a final salt concentration ranging from 5 to 200 mM and a final β-lactoglobulin concentration of 1%. Subsequent heat treatment (80° C., 10 min, about 2 min heating up) was carried out to produce micelles.

The results are shown in FIG. 4 and clearly indicate that only in the ionic strength range of from about 50 to 70 mM, a substantial turbidity can be observed, indicating the presence of whey protein micelles.

Example 5

Preparing a Whitening Agent

Native whey proteins (WPI 95 batch 848, Lactalis; 8 wt-% aqueous solution) were treated according to example 2. The resulting product lightness (L) was measured in trans-reflectance mode using a MacBeth CE-XTH D65 10° SCE apparatus equipped with a 2 mm measuring cell. The resulting lightness was L=74.8, that could be compared to the value of L=74.5 for full-fat milk.

Example 6

Preparing a Coffee Creamer

Native whey proteins (Bipro®, lot JE 032-1-420, 0.5 wt-% aqueous solution) were mixed at 50° C. with 10 wt.-% partially hydrogenated palm oil, 14 wt. % maltodextrin (DE 21) and in presence of 50 mM phosphate-citrate buffer adjusted to the micellisation pH of 6.0 for this Bipro®. The mixture was homogenized under 400/50 bars using a Rannie homogeniser and subsequently heat-treated for 15 minutes at 85° C.

The emulsion obtained showed a high stability over a time period of at least one month at the conditions of storage at 4° C. and gave a whiteness of L=78 compared to a reference liquid creamer (Crème à Café, Emmi, Switzerland) having a fat content of 15% and a lightness of L=75.9.

Example 7

Preparing an Aqueous Foam

Native β-lactoglobulin (Biopure, Davisco, lot JE 002-8-922, 2 wt-% aqueous solution) was mixed with 120 mM Arginine HCl solution so that the final β-lactoglobulin concentration was 1 wt. % and Arginine HCl 60 mM. The pH was then adjusted to 7.0 by addition of 1N HCl. The mixture was then heat treated at 80° C. for 10 minutes so that 90% of initial β-lactoglobulin was converted into micelles having a z-averaged diameter of 130 nm. In this case, the diameter of the micelles was determined using a Nanosizer ZS apparatus (Malvern Instruments, UK). The sample was poured in a quartz cuvette and variations of the scattered light were recorded automatically. The obtained autocorrelation function was fitted using the cumulants method so that the diffusion coefficient of the particles could be calculated and thereafter the z-averaged hydrodynamic diameter using the Stokes-Einstein law. For this measurement, the refractive index of the solvent was taken as 1.33 and that of the micelles 1.45. A volume of 50 mL of the resulting dispersion of β-lactoglobulin micelles is then foamed by nitrogen sparging through a glass frit generating bubbles of 12-16 μm to produce a foam volume of 180 cm$^3$ using the standardised Foamscan™ (ITConcept) apparatus. The volume stability of the foam was then followed with time at 26° C. using image analysis and compared to the stability of the foam obtained with β-lactoglobulin treated in the same conditions, but without Arginine HCl, where no micelles were formed. FIG. 5 shows that the foam volume stability is greatly improved by the presence of β-lactoglobulin micelles.

Example 8

Whey Based Fermented Dairy Product—Fermentation Trials

Material

Whey protein isolate (WPI) (Bipro®) was obtained from Davisco (Le Sueur, Minn., USA) (protein concentration 92.7%). Spray dried whey permeate (Variolac 836): Lactose concentration: 83%—Minerals: 8%

Lactic Acid 50%

Edible Lactose (Lactalis)

De-ionized water

Method

The Bipro® powder was dissolved in de-ionized water in order to have a protein concentration of 4.6%, i.e. for 3 liters of solution 154.5 g of WPI powder and 2845.5 g of water. The hydration time was 3 hours. After hydration, this solution has been divided in samples of 200 ml to prepare the different trials:

TABLE 3

| Trial | Whey permeate (%) | Lactose (%) | pH adjustment | Heating 85° C./15 min |
|---|---|---|---|---|
| 1 | 2.9 | 2.5 | 6.5 | + |
| 2 | 0 | 5 | 6 | + |
| 3 | 0 | 5 | 6.7 | − |
| 4 | 0 | 5 | 6.7 | + |
| 5 | 0 | 5 | 6.1 | + |
| 6 | 0 | 0 | 6 | + |
| 7 | 0 | 5 (added after pH adjustment) | 6 | − |
| 8 | 0 | 5 (added after pH adjustment) | 6 | + |

For each solution, lactic acid at 50% has been added to adjust the pH before heating.

Samples were heated with the double boiler up to 85° C. and maintain at this temperature during 15 minutes. After heating, solutions were cooled at 40° C. and inoculated with *Lactobacillus bulgaricus* and *Streptococcus thermophilus*. Samples stayed 5 h30 in a steam room at 41° C. before to be placed in a cold room at 6° C.

The results are presented in Table 4.

TABLE 4

| Trial | Whey permeate | Lactose | pH | Heating | pH after 5 h 30 | Aspect |
|---|---|---|---|---|---|---|
| 1 | + | + | 6.5 | + | 4.68 | Very firm |
| 2 | − | + | 6 | + | 4.7 | Firm |
| 3 | − | + | 6.7 | − | 5.78 | Liquid |
| 4 | − | + | 6.7 | + | 4.81 | Very firm |
| 5 | − | + | 6.1 | + | 4.59 | Very firm |
| 6 | − | − | 6 | + | 4.99 | Very firm |
| 7 | − | − added after pH adjustment | 6 | − | 4.87 | Liquid with white speckles |
| 8 | − | − added after pH adjustment | 6 | + | 4.77 | Firm |

Example 9

Whey Protein Boosted Ice Cream with Reduced Fat Content

Material

Whey protein isolate (WPI, Prolacta90® from Lactalis, Rétiers, France) with a protein content of 90%

Skim milk powder with 35% protein content

Sucrose

Maltodextrins DE39

Anhydrous milk fat

Emulsifier

De-ionised water

Edible hydrochloric acid 1M

Method

Using a double-jacketed 80 L tank, the Prolacta90® powder was dispersed at 50° C. in de-ionised water at a protein concentration of 9.67 wt % under gentle stirring in order to avoid foam formation, i.e. 3.3 kg of Prolacta90® were dispersed in 31.05 kg of de-ionised water. After 1 hour of dispersion, the pH of the dispersion was adjusted to the micellisation pH by addition of HCl. The temperature of the dispersion was raised to 85° C. and maintained for 15 minutes in order to generate the whey protein micelles. After 15 minutes, the temperature was decreased to 50° C. and the additional ingredients were sequentially added to the micelles dispersion (i.e. skim milk powder, maltodextrins DE39, sucrose, emulsifier and anhydrous milk fat). The final amount of mix was 50 kg with total solids content of 39.5% and a fat content of 5 wt %. After 30 minutes of hydration, the mix was two-step homogenised (80/20 bars) and pasteurised (86° C./30 s) before ageing during overnight.

The day after, the ice-cream mix was frozen at an overrun of 100% using a Hoyer MF50 apparatus and hardened at −40° C. before storage at −20° C. The final ice cream contained 8 wt % proteins (20% caseins, 80% whey proteins) and 5 wt % fat on the ice cream mix basis.

Example 10

Powdered Whey Protein Micelles Obtained by Spray-Drying

Material

Whey protein isolate (WPI, Prolacta90® from Lactalis, Rétiers, France) with a protein content of 90%

Edible lactose

Maltodextrins DE39

De-ionised water

Edible hydrochloric acid 1M

Method

Using a double-jacketed 100 L tank, the Prolacta90® powder was dispersed at 50° C. in de-ionised water at a protein concentration of 10 wt % under gentle stirring in order to avoid foam formation, i.e. 11 kg of Prolacta90® were dispersed in 89 kg of de-ionised water. After 1 hour of dispersion, the pH of the dispersion was adjusted to the micellisation pH (around 6.3 in that case) by addition of HCl. The temperature of the dispersion was raised to 85° C. and maintained for 15 minutes in order to generate the whey protein micelles. After 15 minutes, the temperature was decreased to 50° C. and the 10 wt % whey protein micelles dispersion was split in two batches of 50 kg. In a first trial, 20 kg of lactose were dispersed in 50 kg of micelles dispersion at 50° C. and stirred for 30 min. Similarly, 20 kg of maltodextrins DE39 were added to the remaining 50 kg of whey protein micelles dispersion.

The two mixtures were then spray dried into a NIRO SD6.3N tower at a flow rate of 15 L/h. The air input temperature was 140° C. and the air output temperature was 80° C. The water content of the obtained powders was lower than 5%. The size of the whey protein micelles was determined in presence of lactose and maltodextrin (DE39) in water using dynamic light scattering before and after spray drying. The total protein concentration was set to 0.4 wt % by dilution of the dispersion before spray drying or reconstitution of the powder in order to be in the dilute regime of viscosity for whey protein micelles. A Nanosizer ZS apparatus (Malvern Instruments) was used and micelle diameter was averaged from 20 measurements.

The particle diameter determined for whey protein micelles in presence of lactose and maltodextrins (DE39) was 310.4 nm and 306.6, respectively. After reconstitution of the powders, the respective diameters were found to be 265.3 nm and 268.5, respectively. These measurements confirm than whey protein micelles were physically stable regarding spray drying. The results were corroborated by TEM microscopy observations of 0.1 wt % whey protein micelles dispersions in water using negative staining in presence of 1% phosphotungstic acid at pH 7. A Philips CM12 transmission electron microscope operating at 80 kV was used. Whey protein micelles were observed in solution before spray drying and after reconstitution of the spray-dried powder. No difference of morphology and structure could be detected.

Example 11

Concentration by Evaporation

A whey protein isolate Prolacta 90 from Lactalis (lot 500648) has been reconstituted at 15° C. in soft water at a protein concentration of 4% to reach a final batch size of 2500 kg. The pH was adjusted by addition of 1M hydrochloric acid so that the final pH value was 5.90. The whey protein dispersion was pumped through plate-plate APV-mix heat exchanger at a flow rate of 500 l/h. Pre-heating at 60° C. was followed by heat treatment of 85° C. for 15 minutes. Formation of whey protein micelles was checked by measurement of particle size using dynamic light scattering as well a turbidity measurement at 500 nm. The obtained 4% whey protein micelles dispersion was characterised by a hydrodynamic radius of particles of 250 nm, a polydispersity index of 0.13 and a turbidity of 80. The whey protein micelle dispersion was then used to feed a Scheffers evaporator at a flow rate of 500 l/h. The temperature and vacuum in the evaporator were adapted so that around 500 kg whey protein micelles concentrate having a protein concentration 20% were produced and cooled down to 4° C.

Example 12

Enrichment by Microfiltration

A whey protein isolate Prolacta 90 from Lactalis (lo 500648) has been reconstituted at 15° C. in soft water at a protein concentration of 4% to reach a final batch size of 2500 kg. The pH was adjusted by addition of 1M hydrochloric acid so that the final pH value was 5.90. The whey protein dispersion was pumped through plate-plate APV-mix heat exchanger at a flow rate of 500 l/h. A pre-heating at 60° C. was followed by heat treatment of 85° C. for 15 minutes. Formation of whey protein micelles was checked by measurement of particle size using dynamic light scattering as well a turbidity measurement at 500 nm. The obtained 4% whey protein micelles dispersion was characterised by a hydrodynamic radius of particles of 260 nm, a polydispersity index of 0.07 and a turbidity of 80. The micelle form of the protein was also checked by TEM, and micelle structures with an average diameter of 150-200 nm were clearly visible (FIG. 9). The whey protein micelle dispersion could be cooled at 4° C. for storage or directly used to feed a filtration unit equipped with a 6.8 m² Carbosep M14 membrane at a flow rate of 180 l/h. In that case, the concentration of the whey protein micelles was performed at 10 to 70° C. until the permeate flow rate reached 70 l/h. In that case, the final whey protein concentrate contained 20% of proteins. The structure of the micelles in the concentrate was checked by TEM, and clearly no significant change was visible compared to the 4% whey protein dispersion before microfiltration (FIG. 10).

Example 13

Whey Protein Micelles Powder Comprising at Least 90% Whey Protein 200 kg of a whey protein micelle concentrate obtained by microfiltration at 20% protein (see example above) were injected in a Niro SD6.3N tower using an atomisation nozzle (Ø=0.5 mm, spraying angle=65°, pressure=40 bars) at a product flow rate of 25 kg/h. The inlet temperature of product was 150° C. and the outlet temperature was 75° C. The airflow in the tower was 150 m³/h. The moisture content in the powder was less than 4% and the powder was characterized by a very high flowability. Scanning electron microscopy of the powder exhibited very spherical particles having an apparent diameter ranging from 10 to 100 µm (FIG. 8).

Example 14

Mixed Whey Protein Micelle Powder 20 kg of a whey protein micelle concentrate were mixed with 1.7 kg of maltodextrins with a DE of 39 so that the final whey protein micelle to maltodextrin ratio in powder is 70/30. This mixture was injected in a Niro SD6.3N tower using an atomisation nozzle (Ø32 0.5 mm, spraying angle=65°, pressure=40 bars) at a product flow rate of 25 kg/h. The inlet temperature of product was 150° C. and the outlet temperature was 75° C. The airflow in the tower was 150 m³/h. The moisture content in the powder was less than 4% and the powder was characterized by very high flow ability.

The powders of examples 13 and 14, when reconstituted in water, comprise essentially micelles having the same structure and morphology as the whey protein micelle concentrate.

Example 15

Whey Protein Micelle Powder Obtained by Freeze-Drying

Material
Whey protein micelle concentrate at 20% protein produced by microfiltration in example 12 with a protein content of 90%

Method
100 g of whey protein micelles concentrate were introduced in a plastic beaker and frozen at -25° C. for one week. This beaker was then placed in a lab-scale freeze drier Virtis equipped with a vacuum pump. Sample was left for 7 days until the pressure in the freeze drier remained constant at about 30 mbars. Around 20 g of freeze-dried whey protein micelles has been recovered.

Example 16

A Whey Protein Enriched Dark Chocolate without Sucrose

Material

| Ingredients | Percentage |
| --- | --- |
| Whey protein micelle powder from example 13 with a protein content of 90% | 40-50% |
| Sucralose | 0.05-0.1% |
| Anhydrous milk fat | 3-5% |
| Cocoa liquor | 30-40% |
| Cocoa butter | 5-15% |
| Vanillin | 0.005-0.015% |
| Lecithin | 0.1-1% |

Method
Cocoa liquor is mixed with cocoa butter, butter fat, whey protein micelle powder, sucralose, vanillin and lecithin. This mixture is conched overnight at 65° C. until a homogenous paste is obtained. This chocolate mass is then moulded in chocolate plates and cooled down. The dark chocolate is characterized by a final whey protein content of 45-50%.

Example 17

A Whey Protein Enriched White Chocolate

Material

| Ingredients | Method 1 | Method 2 | Method 3 |
| --- | --- | --- | --- |
| Whey protein micelle powder from example 13 with a protein content of 90% | 15-25% | 25-35% | 35-40% |

-continued

| Ingredients | Method 1 | Method 2 | Method 3 |
|---|---|---|---|
| Sucrose | 40-45% | 30-35% | 30-35% |
| Anhydrous milk fat | 1-10% | 1-10% | 1-10% |
| Whey powder | 2-10% | 2-10% | 0% |
| Cocoa butter | 20-30% | 20-30% | 20-30% |
| Vanillin | 0.01-0.1% | 0.01-0.1% | 0.01-0.1% |
| Lecithin | 0.1-1% | 0.1-1% | 0.1-1% |

Method 1

Whey protein micelles, whey powder, sucrose and vanillin are mixed and ground until the desired particle size distribution is obtained. This mixture is then conched overnight at 65° C. with cocoa butter, anhydrous milk fat and lecithin until a homogenous paste is obtained. This chocolate mass is then moulded in chocolate plates and cooled down. This white chocolate is characterized by a final whey protein content of 20%.

Method 2

Whey protein micelles, whey powder, sucrose and vanillin are mixed and ground until the desired particle size distribution is obtained. This mixture is then conched overnight at 65° C. with cocoa butter, anhydrous milk fat and lecithin until a homogenous paste is obtained. This chocolate mass is then moulded in chocolate plates and cooled down. This white chocolate is characterized by a final whey protein content of 30%.

Method 3

Whey protein micelles, sucrose and vanillin are mixed and ground until the desired particle size distribution is obtained. This mixture is then conched overnight at 65° C. with cocoa butter, anhydrous milk fat and lecithin until a homogenous paste is obtained. This chocolate mass is then moulded in chocolate plates and cooled down. This white chocolate is characterized by a final whey protein content of 30-35%.

Example 18

Aqueous Dispersion of Whey Protein Micelles Coated with Sulfated Butyl Oleate (SBO) or Any Other Negatively Charged Emulsifier Material Whey protein micelle (WPM) powder from example 13 with a protein content of 90%
SBO
Hydrochloric acid (1M)

Method

WPM powder described in example 13 is dispersed in MilliQ water to achieve a final protein concentration of 0.1 wt %. This dispersion is filtered on 0.45 µm filters in order to remove possible WPM aggregates. The pH of this WPM dispersion was brought down to 3.0 by addition of hydrochloric acid 1M. A 1 wt % dispersion of SBO is prepared at pH 3.0.

The hydrodynamic radius and zeta potential of these WPM was determined using the Nanosizer ZS apparatus (Malvern Instruments Ltd.). Diameter was 250 nm and electrophoretic mobility+2.5 $\mu m.cm.V^{-1}.s^{-1}$. The hydrodynamic radius and electrophoretic mobility of the SBO dispersion at pH 3.0 are 4 nm and $-1.5/-2.0$ $\mu m.cm.V^{-1}.s^{-1}$, respectively.

After having performed this preliminary characterization, the SBO dispersion is used to titrate the WPM one, while following evolution of hydrodynamic radius and electrophoretic mobility of the mixture. It was found that the hydrodynamic radius was constant around 250-300 nm until a WPM/SBO weight-mixing ratio of 5:1 was reached. At this point, the hydrodynamic radius diverges dramatically to 20000 nm and precipitation of complexes WPM SBO is encountered. Upon further addition of SBO, higher than a mixing ratio of 5:1, the hydrodynamic progressively decreased to 250 nm, as found initially for WPM, levelling of from a ratio of 4:1 on. Following the electrophoretic mobility of the mixture showed that it decreased upon addition of SBO, reaching zero value for a mixing ratio of 5:1. Then it continued to drop upon SBO addition, starting levelling of at $-3.0$ $\mu m.cm.V^{-1}.s^{-1}$ from ratio 4:1 on.

The explanation for these results is that the positively charged WPM are, in a first step coated electrostatically with the negative head of the SBO until full charge neutralisation is achieved (mixing ratio 5:1). At this point, the hydrophobic tails from the SBO are able to self-associate, leading to over-aggregation with very large hydrodynamic diameter and precipitation of complexes. Upon further addition of SBO, the hydrophobic tails associate further to form a double coating, exposing their negative head to the solvent. This lead to negatively charged WPM with a double coating of SBO (see FIG. 17) comparable to a full protein core liposome.

Similar results have been obtained with other acidic food grade Emulsifiers such as DATEM, CITREM, SSL (from Danisco) in aqueous solution at pH 4.2 where they are mainly ionized in their anionic form ($-COO^-$ chemical functions).

Example 19

A Protein-Enriched Béchamel Sauce

Material

Mixed whey protein micelle powder from example 14 with a protein content of 70%
Butter
Flour
Skim milk
Salt Method 30 g of mixed whey protein powder are dispersed in 1 liter of skim milk under heating. 30 g of butter and 80 g of flour are then added together with 2.85 g of salt. The mixture is then boiled in order to produce a béchamel sauce having a whey protein content of about 3 g/100 g.

Example 20

A Whey Protein-Enriched Base for Performance Bar

Material

| Ingredients | Percentage |
|---|---|
| Mixed whey protein micelle powder from example 13 with a protein content of 90% (moisture 3.5%) | 40-50% |
| Brown rice syrup | 35-45% |
| Maltitol | 5-10% |
| Glycerol | 10-15% |

Method

Brown rice syrup is mixed with maltitol and glycerol at 25° C. Whey protein micelle powder is then added and mixing is performed for 10 minutes. A whey protein-enriched base for performance bar is then obtained and can be mixed with other ingredients (minerals, vitamins, flavours). This preparation contains more proteins than milk (38%).

Example 21

Determination of Repose Angle for Spray Dried Whey Protein Micelle Powder, Mixed Whey Protein Micelle Powder, Whey Protein Isolate Powder and Low Heat Skim Milk Powder Material Whey protein micelle powder from example 12 with a protein content of 90% (moisture 3.5%)

Mixed whey protein micelle powder from example 13 with a protein content of 90% (moisture 3.5%)

Whey protein isolate powder Prolacta 90 (lot 500658 from Lactalis, France; moisture 4%)

Low heat skim milk powder (lot 334314 from Emmi, Switzerland; moisture 3.5%)

Measuring device described to measure repose angle for powders according to ISO norm 4324

Method

The powder is placed in a funnel with a stem diameter of 99 mm and the powder is forced to flow using the agitator. The powder falls on a transparent plastic vessel with diameter 100 mm and a height of 25 mm. The angle of repose, $\phi$, is measured from the following equation:

Repose angle $\phi$=ARCTAN(2 h/100)

Where h is the maximum height of the powder cone than can be obtained, all surface of the plastic vessel being covered with powder.

Results from the repose angle test (values are mean of 3 measurements and standard deviation is indicated).

| | Whey protein micelle powder | Mixed whey protein micelle powder | Whey protein isolate | Low heat skim milk powder |
|---|---|---|---|---|
| Repose angle (°) | 24.6 ± 1.1 | 27.3 ± 0.7 | 34.3 ± 0.5 | 43.8 ± 2.8 |

Repose angle results clearly show that whey protein micelle powder, pure or mixed with maltodextrins, exhibit a significantly lower angle than the initial whey protein powder or even skim milk powder. A repose angle lower than 35° is characteristic of very well flowing powders.

Example 22

Recipe to Obtain a Green Tea Extract Delivery Vehicle

Method 1

5 ml of 20% green tea extract solution were poured on 10 g of pure whey protein micelle powder, then vigorously stirred in a beaker. The powder absorbed all the liquid phase. The residual water was eliminated by drying at 60° C. in an oven during 18 hours. The final product contain 9% green tea extract.

Method 2

30 ml of alcoholic extract of green tea were poured onto 70 g of pure whey micelle powder, then stirred. The final product had a very pleasant green colour. Ethanol was evaporated at ambient temperature.

Example 23

Recipe to Obtain a Caffeine Delivery Vehicle 10 ml of 2% caffeine were poured on 10 g of pure whey protein micelle powder then vigorously stirred in a beaker. The powder absorbed all the liquid phase. Drying at 60° C. in an oven during 18 hours eliminated the residual water. The final product contains 1.7% caffeine. The compact final product was manually crushed and tested. The product was crispy and no bitterness was perceived, even at such high caffeine content.

Example 24

Recipe to Obtain a Coffee Extract Delivery Vehicle 5 ml of solution containing 20% soluble coffee extract were poured on 10 g of pure whey protein micelle powder then vigorously stirred in a beaker. The powder absorbed all the liquid phase. Drying at 60° C. in an oven during 18 hours eliminated the residual water. The final product contains 9% soluble coffee extract, was very crispy and had a strong coffee taste.

Example 25

Recipe to Obtain a Lycopene Delivery Vehicle 30 ml of saturated lycopene alcoholic extract were poured onto 70 g of pure micelle powder, then stirred. The final product had a very pleasant orange colour. Ethanol was evaporated at ambient temperature.

The invention claimed is:

1. Protein micelle aggregates of denatured whey proteins having a molecular size smaller than 1 micron and containing an active agent, with the whey proteins arranged so that hydrophilic parts of the proteins are oriented towards outer parts of the aggregates and hydrophobic parts of the proteins are oriented towards the inner portions of the micelles, wherein the aggregates are obtainable by a method which comprises:
   adjusting the pH of a demineralised native whey protein solution to a value between 5.8 and 6.0, and heating the solution to a temperature of 80° C. to 98° C. for 10 seconds to 2 hours to obtain negatively charged whey protein micelles;
   dispersing the negatively charged whey protein micelles and the active agent in a solvent, and
   evaporating the solvent,
   wherein the whey protein in the micelles is denatured.

2. The protein micelle aggregates according to claim 1, wherein the solvent is selected from the group consisting of water, organic solvents, ethanol, glycerol, and oils.

3. The protein micelle aggregates according to claim 1, wherein the active agent is in a dried form prior to dispersion in the solvent.

4. The protein micelle aggregates according to claim 1, wherein the active agent is in a liquid form prior to dispersion in the solvent.

5. The protein micelle aggregates according to claim 4, wherein the active agent is sprayed onto the whey protein micelles before dispersing in the solvent.

6. The protein micelle aggregates according to claim 1, wherein the evaporation is carried out by spray-drying.

7. Protein micelle aggregates of denatured whey proteins having a molecular size of 100 to 900 nm and containing an active agent, with the whey proteins arranged so that hydrophilic parts of the proteins are oriented towards outer parts of the aggregates and hydrophobic parts of the proteins are oriented towards the inner portions of the micelles, wherein the aggregates are obtainable by a method which comprises:

dispersing native whey protein and an active agent in an aqueous solution having a divalent cation content that is less than 0.2% of the solution, denaturing the whey protein to negatively charged whey protein micelles by adjusting the pH of the aqueous solution to a value of between 5.8 and 6.0 and heating the solution to a temperature of 80° C. to 98° C. for 10 seconds to 2 hours, and forming an aggregate of the negatively charged whey protein micelles and the active agent, wherein the whey protein in the micelles is denatured.

8. Protein micelle aggregates of denatured whey proteins having a molecular size smaller than 1 micron containing an active agent, with the whey proteins arranged so that hydrophilic parts of the proteins are oriented towards outer parts of the aggregates and hydrophobic parts of the proteins are oriented towards the inner portions of the micelles, wherein the aggregates are obtainable by a method which comprises:

(a) adjusting the pH of a demineralised native whey protein solution to a value of between 5.8 and 6.0 and heating the solution to a temperature of 80° C. to 98° C. for 10 seconds to 2 hours to obtain negatively charged whey protein micelles, and (b) mixing a whey protein micelle powder obtainable from the negatively charged whey protein micelles obtained in step (a) with an active agent, wherein the whey protein in the micelles is denatured.

9. The protein micelle aggregates according to claim 8, wherein the active agent is in a solvent prior to mixing.

10. The protein micelle aggregates according to claim 9, wherein the solvent is selected from the group consisting of water, an organic solvent, ethanol, glycerol, and an oil.

11. The protein micelle aggregates according to claim 8, wherein the whey protein micelle powder has a binding capacity of at least 30% for the solvent.

12. The protein micelle aggregates according to claim 7, wherein the whey protein micelle powder comprises at least 50% micelles.

13. The protein micelle aggregates according to claim 8, wherein the active agent is selected from the group consisting of vitamins, minerals, antioxidants, poly-unsaturated fatty acids, peptides, plant extracts, protein hydrolysates, bioactives, aroma, sweeteners, sugars, polysaccharides, sucrose, supplements, pharmaceuticals, drugs, cosmetic components, polyphenols, lycopene, carotenoids, caffeine, hesperidins, soluble or non-soluble salts, probiotic bacteria, stains, maltodextrins, fats, emulsifiers, ligands and any mixtures thereof.

14. The protein micelle aggregates according to claim 8, wherein the active agent is selected from components sensitive to heat, UV radiation, light, oxygen, metals, humidity, or temperature.

15. The protein micelle aggregates according to claim 8, wherein the proportion of micelles to active agent is between 1:1 to 1:1000 and the aggregates have a molecular size of 100-700 nm.

16. The protein micelle aggregates according to claim 8, in the form of a whey protein micelle matrix with at least one active agent incorporated in the matrix.

17. The protein micelle aggregates according to claim 16, wherein the matrix forms an amorphous polymer.

18. The protein micelle aggregates according to claim 8, wherein the active agent is comprised in the aggregate in an amount of 0.1 to 50% and the aggregates have a molecular size of 100-700 nm.

19. A food or cosmetic product comprising the protein micelle aggregates according to claim 1.

20. A food or cosmetic product comprising the protein micelle aggregates according to claim 7.

21. A food or cosmetic product comprising the protein micelle aggregates according to claim 8.

22. The protein micelle aggregates according to claim 1, wherein more than 80% micelles having dimensions between 100-700 nm.

23. The protein micelle aggregates according to claim 1, wherein the whey proteins do not undergo any hydrolysis prior to micelle formation.

* * * * *